(12) United States Patent
Zhang

(10) Patent No.: US 12,229,220 B2
(45) Date of Patent: Feb. 18, 2025

(54) SIMILARITY DETERMINING METHOD AND DEVICE, NETWORK TRAINING METHOD AND DEVICE, SEARCH METHOD AND DEVICE, AND ELECTRONIC DEVICE AND STORAGE MEDIUM

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 488 days.

(21) Appl. No.: 17/418,562

(22) PCT Filed: Nov. 6, 2020

(86) PCT No.: PCT/CN2020/127142
§ 371 (c)(1),
(2) Date: Jun. 25, 2021

(87) PCT Pub. No.: WO2021/098534
PCT Pub. Date: May 27, 2021

(65) Prior Publication Data
US 2022/0076052 A1    Mar. 10, 2022

(30) Foreign Application Priority Data
Nov. 22, 2019 (CN) .......................... 201911159185.X

(51) Int. Cl.
*G06F 18/22*        (2023.01)
*G06F 16/903*       (2019.01)
(Continued)

(52) U.S. Cl.
CPC ........ *G06F 18/22* (2023.01); *G06F 16/90335* (2019.01); *G06F 18/213* (2023.01);
(Continued)

(58) Field of Classification Search
CPC ................ G06F 16/3347; G06F 16/56; G06F 16/90335; G06F 18/213; G06F 18/214;
(Continued)

(56) References Cited

U.S. PATENT DOCUMENTS

2013/0311502 A1* 11/2013 Takata ................ G06F 16/5846
707/758
2017/0061250 A1   3/2017 Gao et al.
(Continued)

FOREIGN PATENT DOCUMENTS

CN    107193919 A    9/2017
CN    107562812 A    1/2018
(Continued)

OTHER PUBLICATIONS

A machine translated English version of WO 2018/188240, (Year: 2018).*
(Continued)

*Primary Examiner* — Ruiping Li
(74) *Attorney, Agent, or Firm* — Chiwin Law LLC

(57) ABSTRACT

A method and device of similarity determination, network training, and search, an electronic device, and a storage medium are provided. The data similarity determination method includes: acquiring first data of a first object; mapping the first sub-data as a first semantic representation in a semantic comparison space, where the semantic comparison space enables a similarity between a semantic representation obtained by mapping data of the first modality to the semantic comparison space and a semantic representation obtained by mapping data of the second modality to the semantic comparison space to be computed; acquiring second data of a second object; mapping the second sub-data as a second semantic representation in the semantic comparison space; and calculating a similarity between the first data
(Continued)

and the second data based on at least the first semantic representation and the second semantic representation.

13 Claims, 10 Drawing Sheets

(51) Int. Cl.
| | |
|---|---|
| *G06F 18/213* | (2023.01) |
| *G06F 18/214* | (2023.01) |
| *G06N 3/08* | (2023.01) |
| *G06V 10/94* | (2022.01) |
| *G06V 30/10* | (2022.01) |
| *G06V 30/262* | (2022.01) |
| *G06V 30/40* | (2022.01) |
| *G16H 10/60* | (2018.01) |
| *G16H 30/20* | (2018.01) |

(52) U.S. Cl.
CPC .......... *G06F 18/214* (2023.01); *G06N 3/08* (2013.01); *G06V 10/95* (2022.01); *G06V 30/274* (2022.01); *G06V 30/40* (2022.01); *G16H 10/60* (2018.01); *G16H 30/20* (2018.01); *G06V 30/10* (2022.01)

(58) Field of Classification Search
CPC ........ G06F 18/22; G06N 3/044; G06N 3/045; G06N 3/08; G06V 10/454; G06V 10/753; G06V 10/761; G06V 10/95; G06V 30/10; G06V 30/274; G06V 30/40; G16H 10/60; G16H 30/20; G16H 30/40
See application file for complete search history.

(56) References Cited

U.S. PATENT DOCUMENTS

| | | |
|---|---|---|
| 2019/0347523 A1 | 11/2019 | Rothberg et al. |
| 2020/0019807 A1 | 1/2020 | Ma et al. |
| 2021/0256365 A1 | 8/2021 | Wang et al. |

FOREIGN PATENT DOCUMENTS

| | | |
|---|---|---|
| CN | 108288067 A | 7/2018 |
| CN | 109492666 A | 3/2019 |
| CN | 109783655 A | 5/2019 |
| CN | 109992686 A | 7/2019 |
| CN | 110188209 A | 8/2019 |
| CN | 110188210 A | 8/2019 |
| CN | 111091010 A | 5/2020 |
| WO | 2018188240 A1 | 10/2018 |

OTHER PUBLICATIONS

First Office Action of the corresponding CN201911159185.X (CNOA1) with search report, dated Apr. 27, 2023.
International Search Report & Written Opinion of the corresponding PCT/CN2020/127142 in English only.

\* cited by examiner

SIMILARITY DETERMINING METHOD AND DEVICE, NETWORK TRAINING METHOD AND DEVICE, SEARCH METHOD AND DEVICE, AND ELECTRONIC DEVICE AND STORAGE MEDIUM

CROSS-REFERENCE TO RELATED APPLICATION

This application is a U.S. National Phase Entry of International Application No. PCT/CN2020/127142 filed on Nov. 6, 2020, designating the United States of America and claiming priority to Chinese Patent Application No. 201911159185.X, filed on Nov. 22, 2019. The present application claims priority to and the benefit of the above-identified applications and the above-identified applications are incorporated by reference herein in their entirety.

TECHNICAL FIELD

The embodiments of the present disclosure relate to a method and device of similarity determination, network training, and search, an electronic device, and a storage medium.

BACKGROUND

With the rapid development of medical informatization, electronic medical data is increasing exponentially. Massive electronic medical data provides opportunities for performing big data analysis and mining. For example, for a given patient, a patient similar to the given patient can be found from a large amount of electronic medical data. The diagnosis, treatment, rehabilitation, and other information of these patients similar to the given patient can be used as an important reference in the following aspects: assessing health risks, selecting treatment plans, estimating the length of hospital stay and treatment costs, thus providing personalized medical services for the given patient and improving the quality of medical services. The above-mentioned process of providing personalized medical services by using the information of the similar patient is similar to the process of doctors making clinical decisions after observing a large amount of clinical case data, which has great clinical significance.

SUMMARY

At least one embodiment of the present disclosure provides a data similarity determination method, which comprises: acquiring first data of a first object, where the first data comprises first sub-data of a first modality or a second modality; mapping the first sub-data as a first semantic representation in a semantic comparison space, where the semantic comparison space enables a similarity between a semantic representation obtained by mapping data of the first modality to the semantic comparison space and a semantic representation obtained by mapping data of the second modality to the semantic comparison space to be computed; acquiring second data of a second object, where the second data comprises second sub-data of the first modality or the second modality; mapping the second sub-data as a second semantic representation in the semantic comparison space; and calculating a similarity between the first data and the second data based on at least the first semantic representation and the second semantic representation.

For example, in at least one example of the data similarity determination method, the first modality is a text, and the second modality is an image.

For example, in at least one example of the data similarity determination method, the first data comprises the first sub-data of the first modality and third sub-data of the second modality; the second data comprises the second sub-data of the first modality and fourth sub-data of the second modality; the first object comprises a first characteristic, the first sub-data comprises a first sub-semantic describing the first characteristic, and the third sub-data comprises a third sub-semantic describing the first characteristic; the second object comprises a second characteristic, the second sub-data comprises a second sub-semantic describing the second characteristic, and the fourth sub-data comprises a fourth sub-semantic describing the second characteristic; the method further comprises: mapping the third sub-data as a third semantic representation in the semantic comparison space and mapping the fourth sub-data as a fourth semantic representation in the semantic comparison space; and calculating the similarity between the first data and the second data based on at least the first semantic representation and the second semantic representation, comprises: acquiring the similarity between the first data and the second data based on the first semantic representation, the second semantic representation, the third semantic representation, and the fourth semantic representation.

For example, in at least one example of the data similarity determination method, acquiring the similarity between the first data and the second data based on the first semantic representation, the second semantic representation, the third semantic representation, and the fourth semantic representation, comprises: calculating at least one of a similarity between the first semantic representation and the fourth semantic representation and a similarity between the second semantic representation and the third semantic representation.

For example, in at least one example of the data similarity determination method, acquiring the similarity between the first data and the second data based on the first semantic representation, the second semantic representation, the third semantic representation, and the fourth semantic representation, further comprises: calculating at least one of a similarity between the first semantic representation and the second semantic representation and a similarity between the third semantic representation and the fourth semantic representation.

For example, in at least one example of the data similarity determination method, the similarity between the first data and the second data is equal to a sum of the similarity between the first semantic representation and the fourth semantic representation, the similarity between the second semantic representation and the third semantic representation, the similarity between the first semantic representation and the second semantic representation, and the similarity between the third semantic representation and the fourth semantic representation.

For example, in at least one example of the data similarity determination method, the first semantic representation, the second semantic representation, the third semantic representation, and the fourth semantic representation are all expressed as vectors; a dimension of a vector corresponding to the first semantic representation, a dimension of a vector corresponding to the second semantic representation, a dimension of a vector corresponding to the third semantic representation, and a dimension of a vector corresponding to the fourth semantic representation are equal to each other.

For example, in at least one example of the data similarity determination method, the similarity $f(p_i,p_j)$ between the first data and the second data is obtained by a following expression:

$$f(p_i, p_j) =$$
$$f((t_i, g_i), (t_j, g_j)) = sim_1(t_i, t_j) + sim_2(t_i, g_j) + sim_2(g_i, t_j) + sim_1(g_i, g_j)$$
$$rt_i = NN1(t_i), rg_i = NN2(g_i), rt_j = NN1(t_j), rg_j = NN2(g_j),$$
$$sim_1(t_i, t_j) = \cos(NN1(t_i), NN1(t_j)) = \cos(rt_i, rt_j) = \frac{rt_i^T \cdot rt_j}{|rt_i||rt_j|},$$
$$sim_1(g_i, g_j) = \cos(NN2(g_i), NN2(g_j)) = \cos(rg_i, rg_j) = \frac{rg_i^T \cdot rg_j}{|rg_i||rg_j|},$$
$$sim_2(t_i, g_j) = \cos(NN1(t_i), NN2(g_j)) = \cos(rt_i, rg_j) = \frac{rt_i^T \cdot rg_j}{|rt_i||rg_j|},$$
$$sim_2(g_i, t_j) = \cos(NN2(g_i), NN1(t_j)) = \cos(rg_i, rt_j) = \frac{rg_i^T \cdot rt_j}{|rg_i||rt_j|},$$

where $p_i$ is the first data, $p_j$ is the second data; $t_i$ is the first sub-data, $g_i$ is the third sub-data, $t_j$ is the second sub-data, and $g_j$ is the fourth sub-data; $sim_1(t_i,t_j)$ is a similarity between the first sub-data and the second sub-data; $sim_1(g_i, g_j)$ is a similarity between the third sub-data and the fourth sub-data; $sim_2(t_i,g_j)$ is a similarity between the first sub-data and the fourth sub-data; $sim_2(g_i,t_j)$ is a similarity between the second sub-data and the third sub-data; NN1 refers to mapping a corresponding sub-data by a first neural network, and NN2 refers to mapping a corresponding sub-data by a second neural network; and $rt_i$ is the first semantic representation, $rg_i$ is the third semantic representation, $rt_j$ is the second semantic representation, and $rg_j$ is the fourth semantic representation.

For example, in at least one example of the data similarity determination method, the first sub-data is mapped as the first semantic representation and the second sub-data is mapped as the second semantic representation by using a first neural network; and the third sub-data is mapped as the third semantic representation and the fourth sub-data is mapped as the fourth semantic representation by using a second neural network.

At least one embodiment of the present disclosure also provides a data similarity determination device, which includes: an acquisition module, a mapping module, and a similarity calculation module. The acquisition module is configured to acquire first data of a first object and second data of a second object, the first data comprises first sub-data of a first modality or a second modality and the second data comprises second sub-data of the first modality or the second modality; the mapping module is configured to map the first sub-data as a first semantic representation in a semantic comparison space and map the second sub-data as a second semantic representation in the semantic comparison space, the semantic comparison space enables a similarity between a semantic representation obtained by mapping data of the first modality to the semantic comparison space and a semantic representation obtained by mapping data of the second modality to the semantic comparison space to be computed; and the similarity calculation module is configured to calculate a similarity between the first data and the second data based on at least the first semantic representation and the second semantic representation.

For example, in at least one example of the data similarity determination device, the first data comprises the first sub-data of the first modality and third sub-data of the second modality; the second data comprises the second sub-data of the first modality and fourth sub-data of the second modality; the first object comprises a first characteristic, the first sub-data comprises a first sub-semantic describing the first characteristic, and the third sub-data comprises a third sub-semantic describing the first characteristic; the second object comprises a second characteristic, the second sub-data comprises a second sub-semantic describing the second characteristic, and the fourth sub-data comprises a fourth sub-semantic describing the second characteristic; the mapping module is further configured to map the third sub-data as a third semantic representation in the semantic comparison space and map the fourth sub-data as a fourth semantic representation in the semantic comparison space; and the similarity calculation module is configured to calculate the similarity between the first data and the second data based on the first semantic representation, the second semantic representation, the third semantic representation, and the fourth semantic representation.

For example, in at least one example of the data similarity determination device, the similarity calculation module is configured to: calculate a similarity between the first semantic representation and the fourth semantic representation, a similarity between the second semantic representation and the third semantic representation, a similarity between the first semantic representation and the second semantic representation, and a similarity between the third semantic representation and the fourth semantic representation. The similarity between the first data and the second data is equal to a sum of the similarity between the first semantic representation and the fourth semantic representation, the similarity between the second semantic representation and the third semantic representation, the similarity between the first semantic representation and the second semantic representation, and the similarity between the third semantic representation and the fourth semantic representation.

At least one embodiment of the present disclosure also provides a data similarity determination device, which comprises a processor and a memory. The memory stores computer program instructions which are executed by the processor, and in a case where the computer program instructions are executed by the processor, the processor executes any data similarity determination method provided by at least one embodiment of the present disclosure.

At least one embodiment of the present disclosure also provides a non-transitory storage medium, which comprises computer program instructions stored on the non-transitory storage medium, in a case where the computer program instructions are executed by a processor, the processor executes any data similarity determination method provided by at least one embodiment of the present disclosure.

At least one embodiment of the present disclosure also provides a training method of a neural network used for determining a data similarity, and the training method comprises: acquiring first training data of a training object, where the first training data comprises first training sub-data of a first modality and second training sub-data of a second modality, the training object comprises a training characteristic, the first training sub-data comprises a first training sub-semantic describing the training characteristic, and the second training sub-data comprises a second training sub-semantic describing the training characteristic; mapping the first training sub-data as a first training semantic representation in a semantic comparison space through a first neural network, where the semantic comparison space enables a similarity between a semantic representation obtained by mapping data of the first modality to the semantic comparison space and a semantic representation obtained by mapping data of the second modality to the semantic comparison space to be computed; mapping the second training sub-data as a second training semantic representation in the semantic comparison space through a second neural network; and calculating a similarity between the first training semantic representation and the second training semantic representation, and adjusting parameters of at least one of the first neural network and the second neural network according to the similarity between the first training semantic representation and the second training semantic representation.

For example, in at least one example of the training method, adjusting the parameters of at least one of the first neural network and the second neural network according to the similarity between the first training semantic representation and the second training semantic representation, comprises: calculating a loss function based on the similarity between the first training semantic representation and the second training semantic representation; and minimizing the loss function by adjusting the parameters of at least one of the first neural network and the second neural network.

For example, in at least one example of the training method, the loss function 1 is obtained by a following expression:

$$l = \frac{1}{2}\sum_{i=1}^{M}(1 - sim_2(trt_i, trg_i))^2 = \frac{1}{2}\sum_{i=1}^{M}(1 - \cos(NN1(trt_i), NN2(trg_i)))^2,$$

where $trt_i$ is first training sub-data of an i-th training object, and $trg_i$ is second training sub-data of the i-th training object; $sim_2(trt_i, trg_i)$ is a similarity between the first training sub-data of the i-th training object and the second training sub-data of the i-th training object; NN1 refers to mapping a corresponding training sub-data by using the first neural network, and NN2 refers to mapping a corresponding training sub-data by using the second neural network; $NN1(trt_i)$ is a first training semantic representation of the i-th training object, and $NN2(trg_i)$ is a second training semantic representation of the i-th training object; and minimizing the loss function by adjusting the parameters of at least one of the first neural network and the second neural network, comprises: adjusting the parameters of at least one of the first neural network and the second neural network based on a gradient descent method.

At least one embodiment of the present disclosure also provides a training device of a neural network used for determining a data similarity, and the training device comprises a processor and a memory. The memory stores computer program instructions suitable for execution by the processor, and in a case where the computer program instructions are executed by the processor, the processor executes any training method provided by at least one embodiment of the present disclosure.

At least one embodiment of the present disclosure also provides a similar object search method, which comprises: acquiring first data of a first object; acquiring second data of a plurality of second objects; calculating a similarity between the first object and each second object by using any data similarity determination method provided by at least one embodiment of the present disclosure to obtain a plurality of object similarities; and outputting information of a second object corresponding to an object similarity with a largest value among the plurality of object similarities.

For example, in at least one example of the similar object search method, the similar object search method further comprises: sorting the plurality of second objected based on the plurality of object similarities.

At least one embodiment of the present disclosure also provides a similar object search device, which comprises any data similarity determination device provided by at least one embodiment of the present disclosure.

For example, in at least one example of the similar object search device, the similar object search device further comprises an object database. The object database stores data of a plurality of objects, and provides the data of at least part of the objects to the data similarity determination device as the second data of the plurality of second objects.

For example, in at least one example of the similar object search device, the similar object search device also includes a human-computer interaction interface. The human-computer interaction interface is configured to receive the first data of the first object, and provide the first data to the data similarity determination device; the data similarity determination device is configured to provide the similarity between the first object and each of the second objects as the plurality of object similarities; the human-computer interaction interface is further configured to output the information of the second object corresponding to the object similarity with the largest value among the plurality of object similarities.

For example, in at least one example of the similar object search device, the similar object search device also includes an information transceiver. The information transceiver is configured to receive the first data of the first object from a client, and provide the first data to the data similarity determination device; the data similarity determination device is configured to provide the similarity between the first object and each of the second objects as the plurality of object similarities; the information transceiver is further configured to provide the information of the second object corresponding to the object similarity with the largest value among the plurality of object similarities to the client.

At least one embodiment of the present disclosure also provides a similar object search device, which includes: a human-computer interaction interface and an information transceiver. The human-computer interaction interface is configured to receive first data of a first object, and provide the first data to the information transceiver; the information transceiver is configured to provide the first data to a server; the information transceiver is further configured to receive, from the server, second data of a second object, which have the greatest similarity with the first data of the first object, and provide the second data of the second object to the human-computer interaction interface; the similarity between the first object and each second object is determined by any data similarity determination device provided by at least one embodiment of the present disclosure.

At least one embodiment of the present disclosure also provides a patient similarity determination method, which comprises: acquiring at least one type of medical text data and medical image data of a first patient; acquiring at least one type of medical text data and medical image data of a second patient; mapping one of the medical text data of the first patient and the medical image data of the first patient as a first semantic representation in a semantic comparison space, where the semantic comparison space enables a similarity between a semantic representation obtained by mapping data of a medical image to the semantic comparison space and a semantic representation obtained by mapping data of a medical text to the semantic comparison space to be capable of being computed; mapping one of the medical text data of the second patient and the medical image data of the second patient as a second semantic representation in the semantic comparison space; and calculating a similarity between the first patient and the second patient based on at least the first semantic representation and the second semantic representation.

For example, in at least one example of the patient similarity determination method, acquiring at least one type of the medical text data and the medical image data of the first patient comprises: acquiring the medical image data of the first patient and the medical text data of the first patient; acquiring at least one type of the medical text data and the medical image data of the second patient comprises: acquiring the medical image data of the second patient and the medical text data of the second patient; mapping one of the medical text data of the first patient and the medical image data of the first patient as the first semantic representation in the semantic comparison space comprises: mapping the medical text data of the first patient as the first semantic representation in the semantic comparison space; mapping one of the medical text data of the second patient and the medical image data of the second patient as the second semantic representation in the semantic comparison space comprises: mapping the medical text data of the second patient as the second semantic representation in the semantic comparison space; the patient similarity determination method further comprises: mapping the medical image data of the first patient as a third semantic representation in the semantic comparison space, and mapping the medical image data of the second patient as a fourth semantic representation in the semantic comparison space; the medical text data of the first patient and the medical image data of the first patient both comprise a semantic describing a first characteristic of the first patient, and the medical text data of the second patient and the medical image data of the second patient both comprise a semantic describing a second characteristic of the second patient; and calculating the similarity between the first patient and the second patient based on at least the first semantic representation and the second semantic representation, comprises: acquiring the similarity between the first patient and the second patient based on the first semantic representation, the second semantic representation, the third semantic representation, and the fourth semantic representation.

For example, in at least one example of the patient similarity determination method, acquiring the similarity between the first patient and the second patient based on the first semantic representation, the second semantic representation, the third semantic representation, and the fourth semantic representation, comprises: calculating at least one of a similarity between the first semantic representation and the fourth semantic representation and a similarity between the second semantic representation and the third semantic representation.

For example, in at least one example of the patient similarity determination method, the similarity between the first patient and the second patient is equal to a sum of a similarity between the first semantic representation and the fourth semantic representation, a similarity between the second semantic representation and the third semantic representation, a similarity between the first semantic representation and the second semantic representation, and a similarity between the third semantic representation and the fourth semantic representation.

For example, in at least one example of the patient similarity determination method, the medical text data of the first patient is mapped as the first semantic representation and the medical text data of the second patient is mapped as the second semantic representation by using a first neural network; and the third sub-data is mapped as the medical image data of the first patient and the medical image data of the second patient is mapped as the fourth semantic representation by using a second neural network.

At least one embodiment of the present disclosure also provides a training method of a neural network used for a patient similarity determination method, and the training method comprises: acquiring medical text data and medical image data of a training patient, where both the medical image data of the training patient and the medical text data of the training patient comprise a training sub-semantic describing a training characteristic of the training patient; mapping the medical text data of the training patient as a first training semantic representation in a semantic comparison space through a first neural network, where the semantic comparison space enables a similarity between a semantic representation obtained by mapping data of a medical text to the semantic comparison space and a semantic representation obtained by mapping data of a medical image to the semantic comparison space to be computed; mapping the medical image data of the training patient as a second training semantic representation in the semantic comparison space through a second neural network; and calculating a similarity between the first training semantic representation and the second training semantic representation, and adjusting parameters of at least one of the first neural network and the second neural network according to the similarity between the first training semantic representation and the second training semantic representation.

At least one embodiment of the present disclosure also provides a similar patient search method, which comprises: acquiring at least one type of medical text data and medical image data of a first patient; acquiring at least one type of medical text data and medical image data of each of a plurality of second patients; calculating a similarity between the first patient and each second patient by using any patient similarity determination method provided by at least one embodiment of the present disclosure to obtain a plurality of patient similarities; and outputting information of a second patient corresponding to a patient similarity with a largest value among the plurality of patient similarities.

At least one embodiment of the present disclosure also provides an electronic device, which comprises a processor and a memory. The memory stores computer program instructions which are executed by the processor, and in a case where the computer program instructions are executed by the processor, the processor executes at least one of any patient similarity determination method provided by at least one embodiment of the present disclosure, any training method provided by at least one embodiment of the present disclosure, and any similar patient search method provided by at least one embodiment of the present disclosure.

BRIEF DESCRIPTION OF THE DRAWINGS

In order to clearly illustrate the technical solutions of the embodiments of the disclosure, the drawings of the embodiments will be briefly described in the following; it is obvious that the described drawings are only related to some embodiments of the disclosure and thus are not limitative to the disclosure.

DETAILED DESCRIPTION

In order to make objects, technical solutions, and advantages of the embodiments of the present disclosure apparent, the technical solutions of the embodiments of the present disclosure will be described in a clearly and fully understandable way in connection with the drawings related to the embodiments of the present disclosure. Apparently, the described embodiments are just a part but not all of the embodiments of the present disclosure. Based on the described embodiments of the present disclosure, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. Similarly, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the absolute position of the object which is described is changed, the relative position relationship may be changed accordingly.

Artificial Intelligence (AI) involves the theory, method, technology, and application system that use digital computers or machines controlled by digital computers to simulate, extend, and expand human intelligence to perceive environment, acquire knowledge, and use knowledge to obtain results. Among algorithm technologies in the AI field, deep learning is widely concerned by academia and industry. With the breakthrough of the deep learning in fields of image classification, target detection, and natural language processing, the demand for applying the deep learning to real life scenarios is also becoming stronger.

Convolution Neural Network (CNN) can be used to recognize two-dimensional shapes. CNN mainly simplifies the complexity of a neural network model and reduces the number of weights by sharing local perception fields and weights. With the development of deep learning technology, CNN has been applied not only in a field of image recognition, but also in fields of face recognition, character recognition, animal classification, image processing, and so on.

Figure 1A:
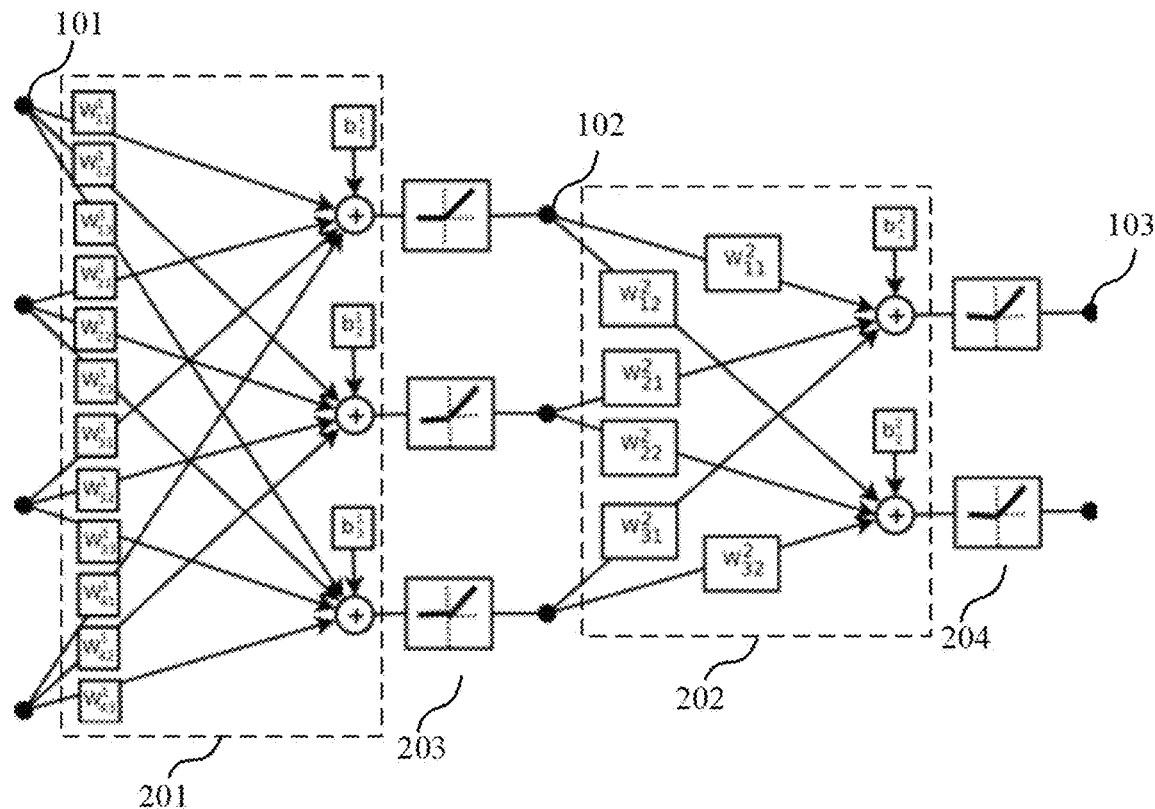
FIG. 1A shows a schematic diagram of a convolution neural network.

FIG. 1A shows a schematic diagram of a convolution neural network. For example, the convolution neural network can be used for image processing, and the convolution neural network uses images as input and output, and replaces scalar weights by convolution kernels. FIG. 1A only shows a convolution neural network with a three-layer structure, the embodiments of the present disclosure are not limited to this case. As shown in FIG. 1A, the convolution neural network includes an input layer 101, a hidden layer 102, and an output layer 103. The input layer 101 has four inputs, the hidden layer 102 has three outputs, and the output layer 103 has two outputs. Finally, the convolution neural network finally outputs two images.

For example, the four inputs of the input layer 101 may be four images or four feature images of one image. The three outputs of the hidden layer 102 may be feature images of the images input through the input layer 101.

For example, as shown in FIG. 1A, the convolution layer has a weight $w_{ij}^k$ and a bias $b_i^k$. The weight $w_{ij}^k$ indicates a convolution kernel, and the bias $b_i^k$ is a scalar added to the output of the convolution layer, where k is a label indicating the input layer 101, and i and j are a label of the input layer 101 and a label of the hidden layer 102. For example, a first convolution layer 201 includes a first group of convolution kernels ($w_{ij}^1$ in FIG. 1A) and a first group of biases ($b_i^1$ in FIG. 1A). A second convolution layer 202 includes a second group of convolution kernels ($w_{ij}^2$ in FIG. 1A) and a second group of biases ($b_i^2$ in FIG. 1A). Generally, each convolution layer includes tens or hundreds of convolution kernels, if the convolution neural network is a deep convolution neural network, the convolution neural network can include at least five convolution layers.

For example, as shown in FIG. 1A, the convolution neural network further includes a first activation layer 203 and a second activation layer 204. The first activation layer 203 is located behind the first convolution layer 201, and the second activation layer 204 is located behind the second convolution layer 202. The activation layers (e.g., the first activation layer 203 and the second activation layer 204) include an activation function, the activation function is used to introduce nonlinear factors into the convolution neural network, so that the convolution neural network can better solve more complex problems. The activation function can include a rectified linear unit (ReLU) function, a S-type function (sigmoid function), or hyperbolic tangent function (tanh function), and the like. The ReLU function is an unsaturated nonlinear function, and the sigmoid function and the tanh function are saturated nonlinear functions. For example, the activation layer can be used as a layer of a convolution neural network alone, or the activation layer can also be included in the convolution layer (for example, the first convolution layer 201 can include the first activation layer 203, and the second convolution layer 202 can include the second activation layer 204).

For example, in the first convolution layer 201, firstly, several convolution kernels $w_{ij}^1$ in the first group of convolution kernels and several biases $b_i^1$ in the first group of biases are applied to each input to obtain the output of the first convolution layer 201; then, the output of the first convolution layer 201 can be processed by the first activation layer 203 to obtain the output of the first activation layer 203. In the second convolution layer 202, firstly, several convolution kernels $w_{ij}^2$ in the second group of convolution kernels and several biases $b_i^2$ in the second group of biases are applied to the output, which is input, of the first activation layer 203 to obtain the output of the second convolution layer 202; then, the output of the second convolution layer 202 can be processed by the second activation layer 204 to obtain the output of the second activation layer 204. For example, the output of the first convolution layer 201 may be the result of applying a convolution kernel $w_{ij}^1$ to the input of the first convolution layer 201 and then adding the input to a bias $b_i^1$, and the output of the second convolution layer 202 may be the result of applying a convolution kernel $w_{ij}^2$ to the output of the first activation layer 203 and then adding the output to a bias $b_i^2$.

The convolution neural network needs to be trained before performing the image processing through the convolution neural network. After training the convolution neural network, the convolution kernels and the biases of the convolution neural network remain unchanged during the image processing. In the training process, each convolution kernel and each bias are adjusted by a plurality of groups of input/output sample images and optimization algorithm to obtain an optimized convolution neural network model.

Figure 1B:
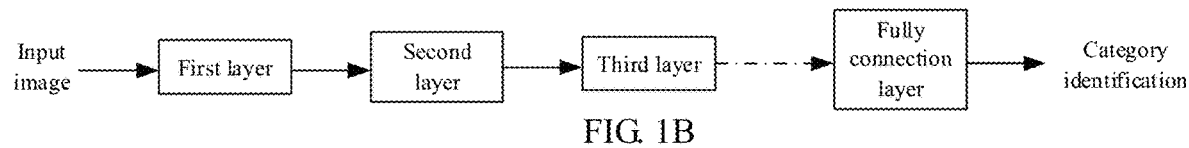
FIG. 1B is a structural schematic diagram of a convolution neural network.
Figure 1C:
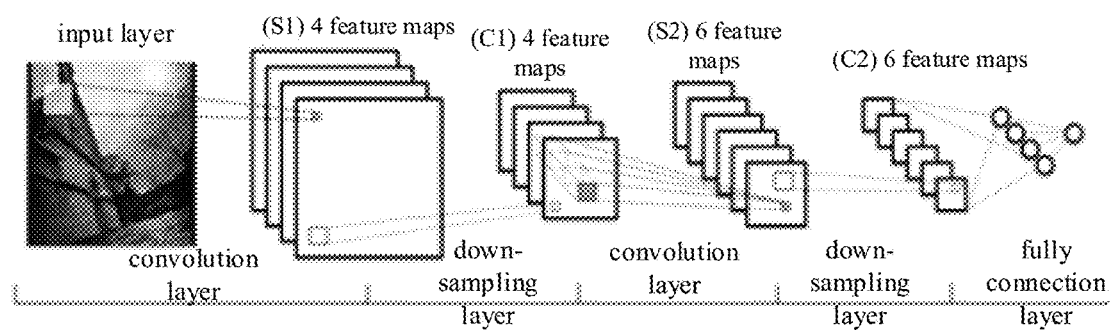
FIG. 1C is a schematic diagram of a working process of a convolution neural network.

FIG. 1B is a structural schematic diagram of a convolution neural network; FIG. 1C is a schematic diagram of a working process of a convolution neural network. For example, as shown in FIG. 1B, the convolution neural network includes a first layer, a second layer, a third layer, a fully connection layer, and the like.

For example, as shown in FIG. 1B and FIG. 1C, after the input image is input to the convolution neural network through the input layer, several processing processes (for example, the first layer, the second layer, and the third layer shown in FIG. 1B) are performed on the input image in turn, and then a category identification is output.

It should be noted that although FIG. 1B only shows that the convolution neural network includes three layers (i.e., the first layer, the second layer, and the third layer), the embodiments of the present disclosure are not limited to this case. For example, the convolution neural network may also include two layers, four layers, or other suitable number of layers.

For example, as shown in FIGS. 1B and 1C, each of a group consisting of the first layer, the second layer, and the third layer may include a convolution module and a down-sampling layer, that is, the main components of the convolution neural network may include a plurality of convolution layers, a plurality of down-sampling layers, and the fully connection layer. For example, the processing at each layer may include performing convolution and sub-sampling/down-sampling on the input image.

The convolution layer is a core layer of the convolution neural network. In the convolution layer of the convolution neural network, a neuron is only connected with neurons in some of adjacent layers. The convolution layer can apply several convolution kernels (also called filters) to the input image to extract various types of features of the input image. Each convolution kernel can extract one type of feature. The convolution kernel is usually initialized in the form of a random decimal matrix. In the training process of the convolution neural network, the convolution kernel gets reasonable weights by learning. The result obtained after applying a convolution kernel to the input image is called a feature map, and the number of feature maps is equal to the number of convolution kernels. Each feature map is composed of some neurons arranged in a rectangle, and the neurons in the same feature map share weights, the weights, which are shared here, are the convolution kernels. The feature map output by the convolution layer of one layer can be input to the convolution layer of the next adjacent layer and can be processed again to obtain a new feature map. For example, as shown in FIG. 1B, the convolution layer of the first layer may output a first feature map, and the first feature map is input to the convolution layer of the second layer and processed again to obtain a second feature map.

For example, as shown in FIG. 1C, the convolution layer can use different convolution kernels to convolute the data of a certain local perception field of the input image, and the convolution result is input to the activation layer, and the activation layer calculates according to the corresponding activation function to obtain the feature information of the input image.

For example, as shown in FIGS. 1B and 1C, the down-sampling layer is arranged between adjacent convolution layers, and the down-sampling layer is a form of down-sampling. On one hand, the down-sampling layer can be used to reduce the size of the input image, simplify the complexity of calculation, and reduce the phenomenon of over-fitting to a certain extent; on the other hand, the down-sampling layer can also perform feature compression to extract the main features of the input image. The down-sampling layer can reduce the size of feature maps without changing the number of feature maps. For example, if an input image with a size of 12×12 is sampled by a convolution kernel of 6×6, an output image with a size of 2×2 can be obtained, which means that 36 pixels on the input image are merged to one pixel in the output image. A last downsampling layer or convolution layer of the convolution neural network can be connected to one or more fully connection layers, the fully connection layer is used to connect all the extracted features. The output of the fully connection layer is a one-dimensional matrix, that is, a vector. Each element of the one-dimensional matrix is used to represent the probability that a certain sample belongs to a predetermined category. For example, the one-dimensional matrix output by the fully connection layer has two elements, and the two elements can be used to represent the probability that a chest PET-CT (Positron Emission Computed Tomography-Computer X-ray Tomography) image shows that nodules is on lungs and the probability that the chest PET-CT image shows that no nodules is on the lungs.

In addition, the most exciting breakthrough that the deep learning brings to natural language processing is word embedding. The word embedding technology is to transform words into vectors, that is, to map the words to a semantic space to get the vectors. In this semantic space, the word vectors corresponding to similar words are also similar, so that the similarity between different words can be calculated. For example, the neural network can be used to map the words to a vector space. For example, in the natural language processing applications, the word embedding is used as the input features of the deep learning models.

For example, the word embedding technology can be divided to a word embedding technology based on a statistical method and a word embedding technology based on a language model. For example, the word embedding technology based on the statistical method can be divided to a word embedding technology based on a co-occurrence matrix and a word embedding technology based on singular value decomposition. For example, in the word embedding technology based on the language model, the language model generates the word vectors by training a neural network language model (NNLM), and the word vectors are the incidental output of the language model. For example, the word embedding technology based on the language model includes a word embedding technology based on word2vec. The word2vec, for example, is implemented by using a neural network, and uses a skip-gram model and a continuous bag of words (CBOW) model. For example, the skip-gram model uses a word as an input to predict the context around the word, and the CBOW model uses the context of a word as input to predict the word itself. For example, the training methods of the skip-gram model and the CBOW model can refer to related technologies, and will not be described in detail here.

In addition, the word embedding can be analyzed by using a recurrent neural network (RNN) model, and the obtained word embedding can be input to the RNN for analysis. A long-short-term memory (LSTM) model is a special RNN model, and is proposed to solve the gradient dispersion problem of the RNN model. In the traditional RNN, the training algorithm uses a back propagation through time (BPTT) algorithm. In the case where the time is relatively long, the residuals that need to be returned will decrease exponentially, resulting in slow update of the network weights, which cannot reflect the long-term memory effect of the RNN. Therefore, a storage unit is needed to store the memory. To solve this problem, researchers proposed the LSTM model. The idea of the long-short-term memory model is to replace each hidden unit in the RNN with a cell having a memory function, that is, to replace a small circle in the hidden layer of the RNN network with a block of the LSTM. For example, the long-short-term memory model includes a forgetting gate (for determining which information to continue to pass through the cell), an introduction gate (for determining how much new information is added to the cell), and an output gate (for determining the output). For example, the specific structure and working principle of the long-short-term memory network can refer to related technologies, and will not be described in detail here.

In the research, the inventor of the present disclosure noticed that a key problem of searching for similar objects is how to calculate (for example, accurately calculate) a similarity between two objects when comprehensively analyzing different types of data. Hereinafter, a case of searching for the similar patients in the analysis of medical related data is taken as an example to describe.

The key problem of searching for the similar patients is how to obtain the similarity between two patients. One way to obtain the similarity between two patients is to calculate the similarity between the data, which is in a single modality, of two patients. For example, the similarity of two patients is obtained by calculating the similarity between the text information recorded in the electronic medical records of two patients; and for another example, the similarity of two patients is obtained by calculating the similarity between the image data of two patients (e.g., computerized X-ray tomography (CT) images, X-ray scanning images, nuclear magnetic resonance images, etc.).

In the research, the inventor of the present disclosure also noticed that in theory, the electronic medical record data and the image data generated for the same patient in the same visit have semantic consistency. For example, a patient's medical record has the following description: "A nodule with a clear boundary can be seen in an upper left lung, and the size of the nodule is 2.2 cm*1.4 cm"; the patient's chest PET-CT (Positron Emission Computed Tomography-Computer X-ray Tomography) image also shows nodules in the upper left lung. At this time, the medical record data and the image data describe the same objective fact, that is, they have semantic consistency. However, because the electronic medical record data and the image data generated for the same patient in the same visit describe the patient's condition in different modalities and ways (i.e., using word and images respectively), the electronic medical record data and the image data generated for the same patient in the same visit have information complementarity. In addition, the electronic medical record data and the image data can also verify and recheck the information provided by each other.

In the research, the inventor of the present disclosure also noticed that because the related patient similarity calculation method obtains the similarity between two patients by calculating the similarity between the data of two patients in the single modality, the patient similarity calculation method cannot utilize the information complementarity of data in different modalities and/or the characteristics of data in different modalities to verify and recheck each other, so the accuracy of the patient similarity calculation result may be low. Accordingly, the searching performance of the similar patient search method based on the above-mentioned patient similarity calculation method may be poor (for example, the searched similar patient may not be the patient most similar to a given patient).

At least one embodiment of the present disclosure provides a data similarity determination method, a data similarity determination device, a non-transitory storage medium, a training method and device of a neural network used for determining a data similarity, a similar object search method, a patient similarity determination method, a training method of a neural network used for a patient similarity determination method, a similar patient search method, and an electronic device. The data similarity determination method comprises: acquiring first data of a first object, where the first data comprises first sub-data of a first modality or a second modality; mapping the first sub-data as a first semantic representation in a semantic comparison space, where the semantic comparison space enables a similarity between a semantic representation obtained by mapping data of the first modality to the semantic comparison space and a semantic representation obtained by mapping data of the second modality to the semantic comparison space to be capable of being calculated; acquiring second data of a second object, where the second data comprises second sub-data of the first modality or the second modality; mapping the second sub-data as a second semantic representation in the semantic comparison space; and calculating a similarity between the first data and the second data based on at least the first semantic representation and the second semantic representation. The data similarity determination method improves the accuracy of the calculation result of the data similarity. For example, the semantic comparison space can be a semantic space, in the semantic space, semantic representations can be compared to calculate a similarity between the semantic representations.

The data similarity determination method, the data similarity determination device, the non-transitory storage medium, the training method and device of a neural network used for determining the data similarity, the similar object search method and device, the patient similarity determination method, the training method of a neural network used for a patient similarity determination method, the similar patient search method, and the electronic device, which are provided by the embodiments of the present disclosure, will be described in a non-limiting manner through several examples and embodiments. As described below, different features in these specific examples and embodiments can be combined with each other without conflicting with each other, so as to obtain new examples and embodiments, these new examples and embodiments also belong to the protection scope of the present disclosure.

It should be noted that, for the sake of clarity, the data similarity determination method provided by at least one embodiment of the present disclosure will be exemplified by taking patient data as an example, but the data similarity determination method provided by at least one embodiment of the present disclosure is not limited to be applied to the similarity of the patient data. For example, the data similarity determination method provided by at least one embodiment of the present disclosure can also be applied to other scenarios involving using different types of data to describe the same or similar characteristics, for example, the similarity of mechanical equipment flaw detection data (including ultrasonic scanning data, optical image data, etc.). Correspondingly, the similar object search method based on the data similarity determination method provided by at least one embodiment of the present disclosure can not only be applied to the search of similar patients, but also can be applied to the search of similar objects in other scenes.

Figure 2:
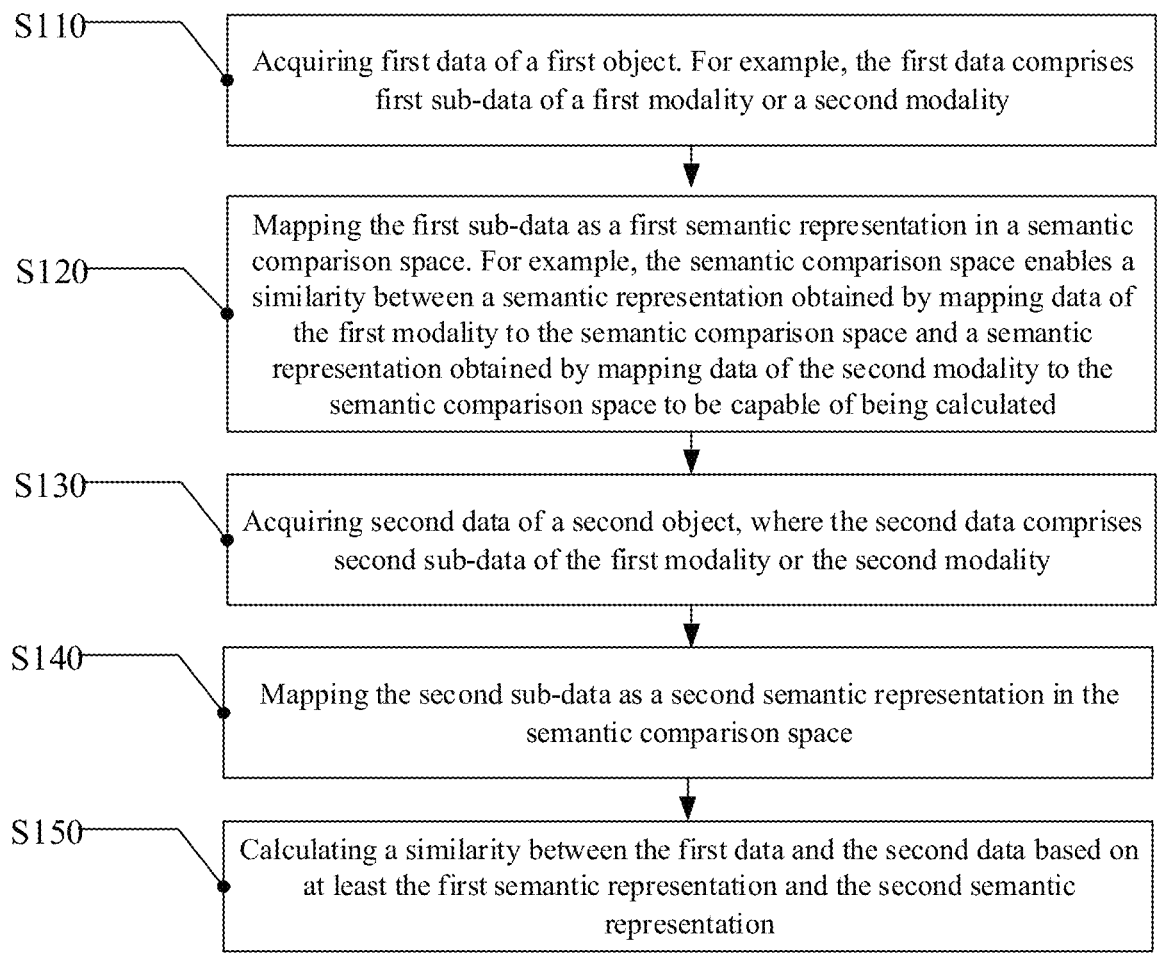
FIG. 2 is a flowchart of a data similarity determination method provided by at least one embodiment of the present disclosure.

FIG. 2 is a flowchart of a data similarity determination method provided by at least one embodiment of the present disclosure. As shown in FIG. 2, the data similarity determination method includes the following steps S110-S150.

S110: acquiring first data of a first object. For example, the first data comprises first sub-data of a first modality or a second modality.

S120: mapping the first sub-data as a first semantic representation in a semantic comparison space. For example, the semantic comparison space enables a similarity between a semantic representation obtained by mapping data of the first modality to the semantic comparison space and a semantic representation obtained by mapping data of the second modality to the semantic comparison space to be capable of being calculated.

S130, acquiring second data of a second object. For example, the second data comprises second sub-data of the first modality or the second modality.

S140: mapping the second sub-data as a second semantic representation in the semantic comparison space.

S150: calculating a similarity between the first data and the second data based on at least the first semantic representation and the second semantic representation.

For example, by mapping the first data of the first object and the second data of the second object to the same semantic space, that is, the semantic comparison space in the embodiment of the present disclosure, that is, in the semantic comparison space where a similarity between the semantic representation obtained by mapping the data of the first modality to the semantic comparison space and the semantic representation obtained by mapping the data of the second modality to the semantic comparison space can be computed, the information complementarity of data of different modalities (for example, using multi-modal fusion) can be used, or data of different modalities are used to verify and recheck each other (for example, data of medical records can be verified and rechecked by using data of images), so that the data similarity determination method provided by at least one embodiment of the present disclosure can improve the accuracy of data similarity calculation results.

For example, the data similarity determination method may be executed in the order of step S110, step S120, step S130, step S140, and step S150, but the embodiments of the present disclosure are not limited thereto. For another example, the data similarity determination method may be executed in the order of step S110+step S130 (i.e., step S110 and step S130 are executed simultaneously), step S120+step S140 (i.e., step S120 and step S140 are executed simultaneously), and step S150.

For example, the first object may be a given patient, that is, a patient currently seeking treatment; the second object is a reference patient to be determined whether it is a similar patient of the given patient, that is, a reference patient who needs to determine the similarity to the given patient.

For example, the first modality is different from the second modality. For example, the first modality is a text, and the second modality is an image (e.g., a picture). For example, the text includes at least one selected from a group consisting of words and numbers. For example, the text includes at least one selected from a group consisting of a text in the medical record and a text related to physiological characteristics provided by a wearable terminal. For example, the text in the medical record can describe the patient's basic information, symptoms, diagnosis results, treatment plans, and so on. For example, the image includes at least one selected from a group consisting of an image related to physiological characteristics provided by a medical imaging equipment and an image related to physiological characteristics provided by the wearable terminal. For example, the image can include a computerized X-ray tomography image, a nuclear magnetic resonance image, an ultrasound image, an electrocardiogram, an electroencephalogram, an optical photography, and other images showing human physiological information. The image can include a static or dynamic image. For example, a video image can be taken as an image including a plurality of frames of images.

For example, the neural network can be used to map the first sub-data as a first semantic representation in the semantic comparison space, and the neural network can be used to map the second sub-data as a second semantic representation in the semantic comparison space. For example, in the semantic comparison space (e.g., an n-dimensional space), both the first semantic representation and the second semantic representation are expressed as vectors (correspondingly, n-dimensional vectors), and the vector corresponding to the first semantic representation and the vector corresponding to the second semantic representation have the same dimension, so the similarity between the first semantic representation and the second semantic representation can be calculated based on the values of the two vectors, which correspond to the first semantic representation and the second semantic representation, in each dimension.

For example, the semantic comparison space can be an n-dimensional Euclidean space, in n-dimensional Euclidean space, an inner product and a distance between vectors can be calculated, as a result, the Euclidean space enables a similarity between a semantic representation obtained by mapping the data of the first modality to the Euclidean space and a semantic representation obtained by mapping the data of the second modality to the Euclidean space to be computed. For example, the neural network can map the data of the first modality and the data of the second modality, which have a high similarity, to neighboring regions of the Euclidean space, and enable vectors obtained by mapping the data of the first modality and vectors obtained by mapping the data of the second modality to have the same dimension.

In an example, the first data of the first object includes first sub-data of the first modality and third sub-data of the second modality; the second data of the second object includes second sub-data of the first modality and fourth sub-data of the second modality; the first object includes a first characteristic, the first sub-data includes a first sub-semantic describing the first characteristic, and the third sub-data includes a third sub-semantic describing the first characteristic; the second object includes a second characteristic, the second sub-data includes a second sub-semantic describing the second characteristic, and the fourth sub-data includes a fourth sub-semantic describing the second characteristic.

In the above example, the data similarity determination method further includes mapping the third sub-data as a third semantic representation in the semantic comparison space, and mapping the fourth sub-data as a fourth semantic representation in the semantic comparison space.

In the above example, calculating the similarity between the first data and the second data based on at least the first semantic representation and the second semantic representation includes: acquiring the similarity between the first data and the second data based on the first semantic representation, the second semantic representation, the third semantic representation, and the fourth semantic representation.

Figure 3A:
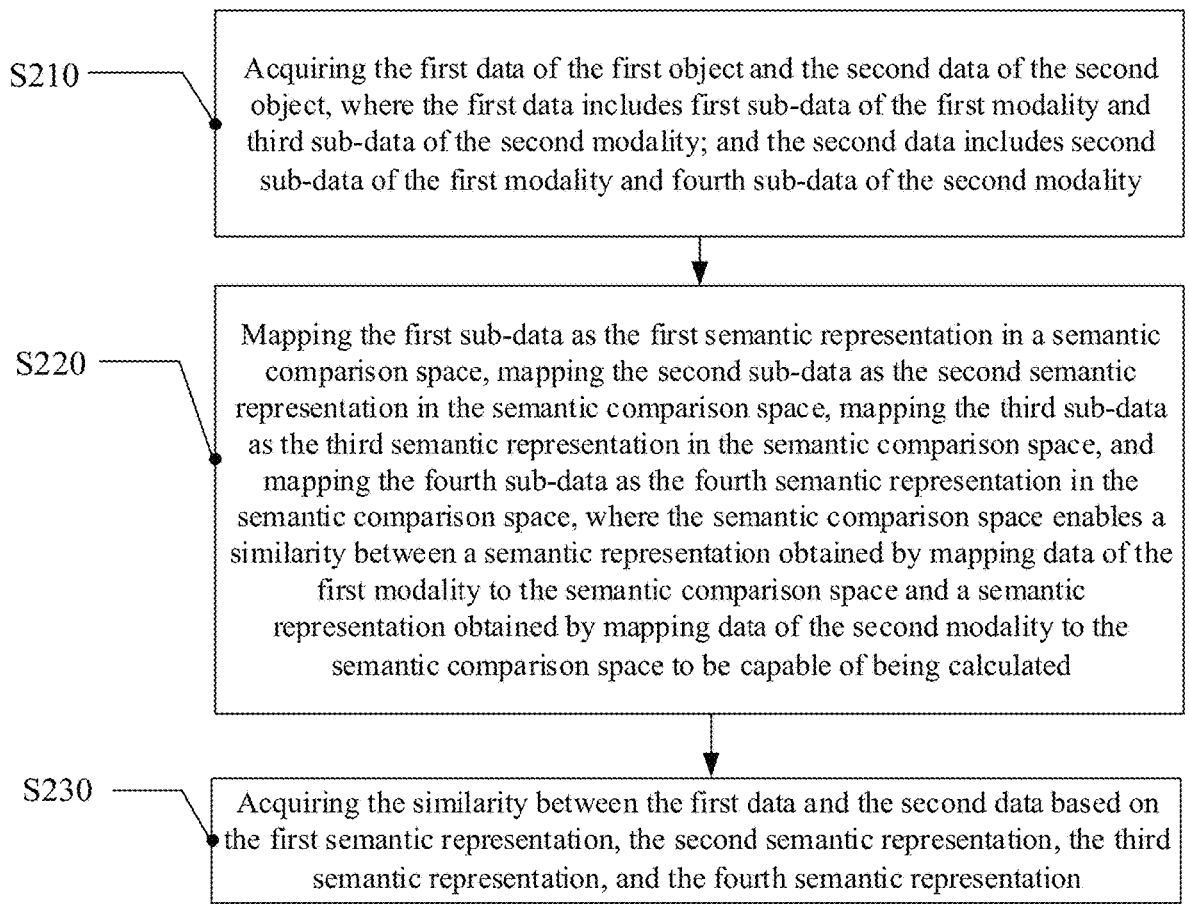
FIG. 3A is a flowchart of an example of the data similarity determination method shown in FIG. 2.

FIG. 3A is a flowchart of an example of the data similarity determination method shown in FIG. 2. As shown in FIG. 3A, the data similarity determination method includes the following steps S210 to S230.

S210: acquiring the first data of the first object and the second data of the second object.

For example, the first object may be a given patient, that is, a patient currently seeking treatment; the second object is a reference patient to be determined whether it is a similar patient of the given patient, that is, a reference patient who needs to determine the similarity to the given patient.

For example, the first data includes first sub-data of the first modality and third sub-data of the second modality; and the second data includes second sub-data of the first modality and fourth sub-data of the second modality.

For example, the first modality is a text and the second modality is an image. In this case, the first data includes first sub-data which is a text and third sub-data which is an image; the second data includes second sub-data which is a text and fourth sub-data which is an image.

For example, the first object includes a first characteristic, the first sub-data includes a first sub-semantic describing the first characteristic, and the third sub-data includes a third sub-semantic describing the first characteristic. The second object includes a second characteristic, the second sub-data includes a second sub-semantic describing the second characteristic, and the fourth sub-data includes a fourth sub-semantic describing the second characteristic. For example, both the first characteristic and the second characteristic are characteristics that describe the same aspect of the object. For example, the first characteristic describes lung-related characteristics of the given patient, and the second characteristic describes lung-related characteristics of the reference patient.

For example, the first sub-semantic and the third sub-semantic describe the first characteristic based on the first modality and the second modality, respectively, and the second sub-semantic and the fourth sub-semantic describe the second characteristic based on the first modality and the second modality. For example, the first sub-semantic of the first sub-data includes the following description: "A nodule with a clear boundary can be seen in the upper left lung, and the size of the nodule is 2.2 cm*1.4 cm"; the third sub-semantic of the third sub-data includes a part of the chest PET-CT (Positron Emission Computed Tomography-Computer X-ray Tomography) image showing nodules in the upper left lung.

S220: mapping the first sub-data as the first semantic representation in a semantic comparison space, mapping the second sub-data as the second semantic representation in the semantic comparison space, mapping the third sub-data as the third semantic representation in the semantic comparison space, and mapping the fourth sub-data as the fourth semantic representation in the semantic comparison space.

For example, the first semantic representation, the second semantic representation, the third semantic representation, and the fourth semantic representation are all expressed as vectors, that is, the first semantic representation, the second semantic representation, the third semantic representation, and the fourth semantic representation are all vectors in the semantic comparison space and have the same dimension, and therefore, the similarity between different semantic representations can be calculated based on the sizes (value) of the vectors in each dimension.

For example, a dimension of a vector corresponding to the first semantic representation, a dimension of a vector corresponding to the second semantic representation, a dimension of a vector corresponding to the third semantic representation, and a dimension of a vector corresponding to the fourth semantic representation can be preset according to actual experience.

For example, the dimension of the vector corresponding to the first semantic representation, the dimension of the vector corresponding to the second semantic representation, the dimension of the vector corresponding to the third semantic representation, and the dimension of the vector corresponding to the fourth semantic representation are equal to each other. For example, by enabling the dimension of the vector corresponding to the first semantic representation, the dimension of the vector corresponding to the second semantic representation, the dimension of the vector corresponding to the third semantic representation, and the dimension of the vector corresponding to the fourth semantic representation to equal to each other, a similarity of any two selected from a group consisting of the first semantic representation, the second semantic representation, the third semantic representation, and the fourth semantic representation can be computed.

For example, the first sub-semantic, the second sub-semantic, the third sub-semantic, and the fourth sub-semantic correspond to the first semantic representation, the second semantic representation, the third semantic representation, and the fourth semantic representation, respectively. For example, mapping the first sub-data as the first semantic representation in the semantic comparison space, mapping the second sub-data as the second semantic representation in the semantic comparison space, mapping the third sub-data as the third semantic representation in the semantic comparison space, and mapping the fourth sub-data as the fourth semantic representation in the semantic comparison space includes: mapping the first sub-semantic as the first semantic representation in the semantic comparison space, mapping the second sub-semantic as the second semantic representation in the semantic comparison space, mapping the third sub-semantic as the third semantic representation in the semantic comparison space, and mapping the fourth sub-semantic as the fourth semantic representation in the semantic comparison space.

For example, the semantic comparison space enables (for example, the semantic comparison space combined with a first neural network and a second neural network enables) it possible to calculate the similarity between the semantic representation obtained by mapping the data of the first modality to the semantic comparison space and the semantic representation obtained by mapping the data of the second modality to the semantic comparison space, that is, the semantic comparison space enables it possible to calculate the similarity between data of different modalities in the semantic comparison space. Therefore, the data similarity determination method shown in FIG. 3A can utilize the information complementarity of data of different modalities and/or the characteristics of verifying and rechecking each other for the data of different modalities, so as to improve the accuracy of data similarity calculation results. For example, in the case where the expressions and dimensions of the two data are consistent, the similarity between the two data can be calculated. For example, in the case where two expressions are vectors with the same dimension, the similarity between the two expressions can be calculated. For example, if the semantic comparison space enables the semantic representation obtained by mapping the data of the first modality to the semantic comparison space and the semantic representation obtained by mapping the data of the second modality to the semantic comparison space to be both expressed as vectors, and further enables a dimension of a vector corresponding to the semantic representation obtained by mapping the data of the first modality to the semantic comparison space and a dimension of a vector corresponding to the semantic representation obtained by mapping the data of the second modality to the semantic comparison space to be equal to each other, then a similarity between the semantic representation obtained by mapping the data of the first modality to the semantic comparison space and the semantic representation obtained by mapping the data of the second modality to the semantic comparison space can be calculated.

For example, mapping the first sub-data, the second sub-data, the third sub-data, and the fourth sub-data respectively as the first semantic representation, the second semantic representation, the third semantic representation, and the fourth semantic representation of the semantic comparison space can reduce the dimensions of at least some data, thereby reducing the amount of calculation for calculating the similarity.

In an example, the first sub-data is mapped as the first semantic representation in the semantic comparison space and the second sub-data is mapped as the second semantic representation in the semantic comparison space by using the first neural network, the third sub-data is mapped as the third semantic representation in the semantic comparison space and the fourth sub-data is mapped as the fourth semantic representation in the semantic comparison space by using the second neural network. That is, the first neural network is used to map the sub-data of the first modality to the semantic comparison space, and the second neural network is used to map the sub-data of the second modality to the semantic comparison space. For example, the first neural network is different from the second neural network, so as to map the sub-data of different modalities to the same semantic comparison space; and the first neural network and the second neural network are trained neural networks (for example, the neural networks trained by machine learning).

For example, the first semantic representation $rt_i$, the third semantic representation $rg_i$, the second semantic representation $rt_j$, and the fourth semantic representation $rg_1$ can be obtained by the following expressions:

$$rt_i=NN1(t_i), rg_i=NN2(g_i), rt_j=NN1(t_j), rg_j=NN2(g_j),$$

where $t_i$ is the first sub-data, $g_i$ is the third sub-data, $t_j$ is the second sub-data, $g_j$ is the fourth sub-data, NN1 refers to mapping the corresponding sub-data by using the first neural network, and NN2 refers to mapping the corresponding sub-data by using the second neural network.

For example, the trained first neural network can disassemble the description of the medical record "A nodule with a clear boundary can be seen in an upper left lung, and the size of the nodule is 2.2 cm*1.4 cm" as follows: an organ type is the lung (a corresponding number is 9), the organ has an abnormality (a corresponding number is 2), the abnormality is the nodule (a corresponding number is 4), a location of the abnormality is the upper left (a corresponding number is 1), and a size of the abnormality is 2.2 cm*1.4 cm. In this case, the trained first neural network can convert the contents describing the lung-related characteristics in the medical record into a first vector (9, 2, 4, 1, 2.2, 1.4). For example, the method of converting the text into the vector by the neural network (for example, the neural network of the long-short-term memory network) can refer to the related technologies, and the similar descriptions will not be described in detail here.

For example, the trained second neural network has the function of confirming whether the organ types and organs in the medical images are abnormal; in addition, if there is an abnormality, the trained second neural network can also determine the type, location, and size of the abnormality. For example, the trained second neural network can confirm that the organ type in the chest PET-CT image is the lung (the corresponding number is 9), the organ has the abnormality (the corresponding number is 2), the abnormality is the nodule (the corresponding number is 4), the position of the abnormality in the image is the upper left (the corresponding number is 1), and the size of the abnormality is 2.2 cm*1.4 cm. In this case, the trained second neural network can transform the information provided by the region describing the lung-related characteristics in the chest PET-CT image into a second vector (9, 2, 4, 1, 2.2, 1.4). For example, because the first vector and the second vector are the same, it can be obtained that the similarity between the medical record and the medical image is 1. For example, the method for the neural network (such as the convolution neural network) to identify the type, size, and location of the object in the image can refer to the related technologies, and the similar descriptions will not be described in detail here.

For example, in order to ensure that the sub-data of different modalities can maintain semantic consistency after being mapped to the semantic comparison space, in the mapping process, the positions of sub-data with consistent semantics in the semantic comparison space should be close after the sub-data with consistent semantics is mapped. For example, for the above example that the upper left lung has nodules, assuming that the first semantic representation (two-dimensional vector) obtained by mapping the first sub-data of the text to the semantic comparison space (two-dimensional space) is (1.5, 1.8), the third semantic representation (two-dimensional vector) obtained by mapping the third sub-data of the image to the semantic comparison space should also be (1.5, 1.8) or a vector very close to (1.5, 1.8) (for example, the difference between them according to the comparison algorithm (such as cosine similarity described later) is less than or equal to a predetermined threshold), that is, the positions where sub-data with consistent semantics is mapped to the semantic comparison space should be the same or very close.

For example, the data of the first modality and the data of the second modality describing the same characteristics of a plurality of objects (for example, a plurality of past patients) can be used as training data (or data sets), and the first neural network and the second neural network can be trained based on machine learning, so that the sub-data of different modalities (the sub-data of different modalities corresponding to the same characteristics of the same object) can maintain semantic consistency after being mapped to the semantic comparison space, and thus the relevant parameters of the first neural network and the relevant parameters of the second neural network can be determined. For example, for the specific method of training the first neural network and the second neural network through the machine learning, reference can be made to a training method and device of a neural network for determining the data similarity provided by at least one embodiment of the present disclosure, and the description will not be described in detail here.

In some examples, the data similarity determination method provided by at least one embodiment of the present disclosure may also include related steps of the training method of the neural network for determining the data similarity. For the specific content of the training method of the neural network for determining the data similarity, reference may be made to a training method and device for neural network for determining the data similarity provided by at least one embodiment of the present disclosure, and the repeated parts will not be described in detail here.

For example, in the case where the first modality is the text and the second modality is the image, the first neural network can be long-short-term Memory Network (LSTM) or word2vec, or word2vect+LSTM, etc.; the second neural network may be a convolution neural network (CNN), the embodiments of the present disclosure are not limited to this case, as long as the first neural network and the second neural network can respectively process the data of different modalities to obtain the vectors in the same semantic space, and thus the similarity between the obtained different vectors can be calculated.

S230: acquiring the similarity between the first data and the second data based on the first semantic representation, the second semantic representation, the third semantic representation, and the fourth semantic representation.

In an example, acquiring the similarity between the first data and the second data based on the first semantic representation, the second semantic representation, the third semantic representation, and the fourth semantic representation includes the following steps S231 and S232. For example, step S231 and step S232 are sequentially executed.

S231: calculating the similarity between the first semantic representation and the fourth semantic representation, the similarity between the second semantic representation and the third semantic representation, the similarity between the first semantic representation and the second semantic representation, and the similarity between the third semantic representation and the fourth semantic representation.

For example, the similarity between the first semantic representation and the fourth semantic representation, the similarity between the second semantic representation and the third semantic representation, the similarity between the first semantic representation and the second semantic representation, and the similarity between the third semantic representation and the fourth semantic representation are equal to the similarity between the first sub-data and the fourth sub-data, the similarity between the second sub-data and the third sub-data, the similarity between the first sub-data and the second sub-data, and the similarity between the third sub-data and the fourth sub-data, respectively.

For example, the similarity $sim_1(t_i,t_j)$ between the first sub-data and the second sub-data, the similarity $sim_1(g_i,g_j)$ between the third sub-data and the fourth sub-data, the similarity $sim_2(t_i,g_j)$ between the first sub-data and the fourth sub-data, and the similarity $sim_2(g_i,t_j)$ between the second sub-data and the third sub-data can be calculated using cosine similarity, that is, the similarity between the two sub-data can be evaluated by calculating a cosine value of semantic representations (the vectors) corresponding to the two sub-data. For example, in the case where two vectors have the same direction, the value of the cosine similarity is 1; in the case where an angle between two vectors is 90, the value of the cosine similarity is 0; in the case where two vectors point in completely opposite directions, the value of the cosine similarity is −1, so that the cosine similarity (the cosine value) of two vectors is between −1 and 1, and the larger the cosine similarity (the cosine value) of two vectors, the closer the two vectors are, correspondingly, the higher the similarity of two sub-data corresponding to two vectors. For example, in the case where the cosine similarity is −1, it means that two vectors are negatively correlated. For example, the values of all elements in the vector corresponding to the first sub-data and the vector corresponding to the second sub-data can be positive. In this case, the cosine similarity between the vector corresponding to the first sub-data and the vector corresponding to the second sub-data is between 0 and 1.

For example, the similarity $sim_1(t_i,t_j)$ between the first sub-data and the second sub-data, the similarity $sim_1(g_i,g_j)$ between the third sub-data and the fourth sub-data, the similarity $sim_2(t_i,g_j)$ between the first sub-data and the fourth sub-data, and the similarity $sim_2(g_i,t_j)$ between the second sub-data and the third sub-data can be obtained by using the following expressions:

$$sim_1(t_i, t_j) = \cos(NN1(t_i), NN1(t_j)) = \cos(rt_i, rt_j) = \frac{rt_i^T \cdot rt_j}{|rt_i||rt_j|},$$

$$sim_1(g_i, g_j) = \cos(NN2(g_i), NN2(g_j)) = \cos(rg_i, rg_j) = \frac{rg_i^T \cdot rg_j}{|rg_i||rg_j|},$$

$$sim_2(t_i, g_j) = \cos(NN1(t_i), NN2(g_j)) = \cos(rt_i, rg_j) = \frac{rt_i^T \cdot rg_j}{|rt_i||rg_j|},$$

$$sim_2(g_i, t_j) = \cos(NN2(g_i), NN1(t_j)) = \cos(rg_i, rt_j) = \frac{rg_i^T \cdot rt_j}{|rg_i||rt_j|},$$

where a superscript T represents a transposition of the vector, "||" represents a length of the vector, and "·" represents a dot multiplication between two vectors.

S232: acquiring the similarity between the first data and the second data based on the similarity between the first semantic representation and the fourth semantic representation, the similarity between the second semantic representation and the third semantic representation, the similarity between the first semantic representation and the second semantic representation, and the similarity between the third semantic representation and the fourth semantic representation.

For example, the similarity between the first data and the second data is equal to a sum of the similarity between the first semantic representation and the fourth semantic representation, the similarity between the second semantic representation and the third semantic representation, the similarity between the first semantic representation and the second semantic representation, and the similarity between the third semantic representation and the fourth semantic representation.

For example, the similarity $f(p_i,p_j)$ between the first data $p_i$ and the second data $p_j$ is obtained by the following expression:

$$f(p_i,p_j)=f((t_i,g_i),(t_j,g_j))=sim_1(t_i,t_j)+sim_2(t_i,g_j)+sim_2(g_i,t_j)+sim_1(g_i,g_j).$$

However, embodiments of the present disclosure are not limited thereto. For example, according to practical experience, appropriate weights (between 0 and 1) can be set for the similarity between the first semantic representation and the fourth semantic representation, the similarity between the second semantic representation and the third semantic representation, the similarity between the first semantic representation and the second semantic representation, and the similarity between the third semantic representation and the fourth semantic representation to further improve the accuracy of the similarity between the first data $p_i$ and the second data $p_j$ obtained by calculation.

For example, step S230 is not limited to being implemented by executing step S231 and step S232. In some examples, step S230 can also be implemented by executing the following steps S233 and S234. For example, step S233 and step S234 are sequentially executed.

S233: calculating the similarity between the first semantic representation and the fourth semantic representation and the similarity between the second semantic representation and the third semantic representation.

S234: acquiring the similarity between the first data and the second data based on the similarity between the first semantic representation and the fourth semantic representation and the similarity between the second semantic representation and the third semantic representation. In this case, the similarity between the first data and the second data can be equal to a sum of the similarity between the first semantic representation and the fourth semantic representation and the similarity between the second semantic representation and the third semantic representation, that is, the similarity between the first data and the second data can be obtained only by calculating the sub-data of different modalities.

It should be noted that the specific implementation method of step S230 can be set according to the actual application requirements, the embodiments of the present disclosure are not specifically limited to this case. For example, step S230 includes calculating at least one selected from a group consisting of the similarity between the first semantic representation and the fourth semantic representation and the similarity between the second semantic representation and the third semantic representation. For example, step S230 further includes calculating at least one selected from a group consisting of the similarity between the first semantic representation and the second semantic representation and the similarity between the third semantic representation and the fourth semantic representation.

Figure 3B:
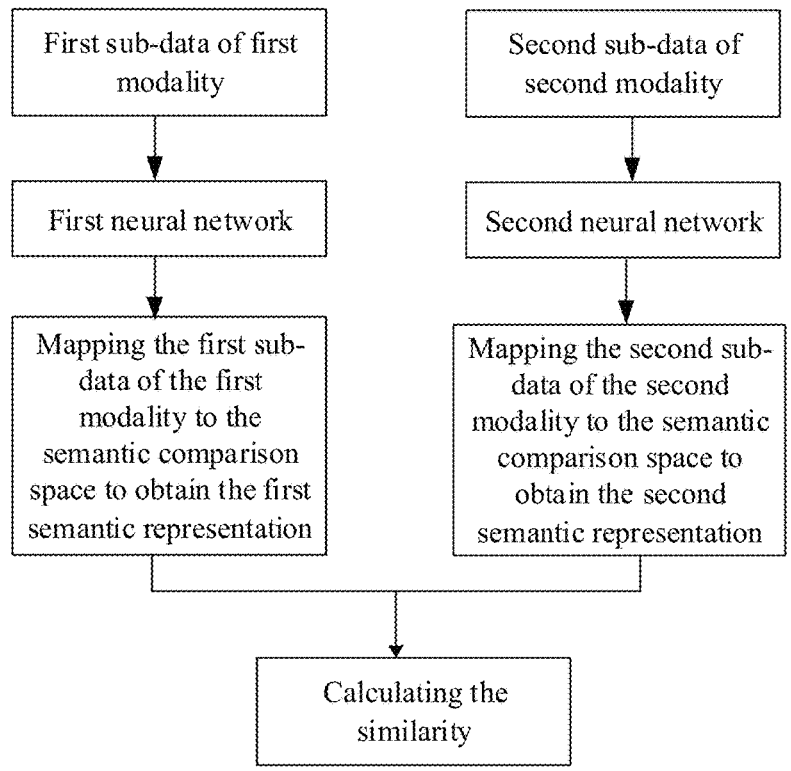
FIG. 3B is a flowchart of another example of the data similarity determination method shown in FIG. 2.

FIG. 3B is a flowchart of another example of the data similarity determination method shown in FIG. 2. As shown in FIG. 3B, the first data of the first object includes the first sub-data of the first modality, and the second data of the second object includes the second sub-data of the second modality. For example, the first modality is a text and the second modality is an image, or the first modality is an image and the second modality is a text.

As shown in FIG. 3B, the first sub-data of the first modality can be mapped to the semantic comparison space to obtain the first semantic representation through the first neural network, and the second sub-data of the second modality can be mapped to the semantic comparison space to obtain the second semantic representation through the second neural network.

For example, in the case where the first modality is the text and the second modality is the image, the first neural network is a long-short-term memory network, or word2vec, or word2vect+LSTM, etc.; the second neural network is a convolution neural network. Similarly, the embodiments of the present disclosure are not limited to this case, as long as the first neural network and the second neural network can respectively process the data of different modalities to obtain vectors in the same semantic space, and thus the similarity between the obtained different vectors can be calculated.

As shown in FIG. 3B, after the first semantic representation and the second semantic representation are obtained, the similarity between the first semantic representation and the second semantic representation is calculated, and the similarity between the first semantic representation and the second semantic representation is taken as the similarity between the first data of the first object and the second data of the second object.

For example, according to actual application requirements, the first data of the first object may also include the third sub-data of the second modality, and the second data of the second object may also include the fourth sub-data of the first modality.

It should be noted that the first data and the second data of the data similarity determination method provided by at least one embodiment of the present disclosure are not limited to the examples shown in FIGS. 3A and 3B. For example, the first data may also include only the first sub-data of the first modality, and the second data may also include only the second sub-data of the second modality. For another example, the first data may also include only the first sub-data of the second modality, and the second data may also include only the second sub-data of the first modality. For another example, the first data includes the first sub-data of the first modality and the third sub-data of the second modality, and the second data only includes the second sub-data of the first modality or the second modality. For another example, the first data only includes the first sub-data of the first modality or the second modality, and the second data includes the second sub-data of the first modality and the fourth sub-data of the second modality. In these examples, the method for calculating the similarity between the first data and the second data can be correspondingly adjusted according to the application requirements, and will not be described in detail here.

It should be noted that any one selected from a group consisting of the first data and the second data of the data similarity determination method provided by at least one embodiment of the present disclosure is not limited to only include sub-data of one or two modalities, and at least one selected from a group consisting of the first data and the second data may also include sub-data of three modalities or other suitable number of modalities according to actual application requirements. For example, at least one selected from a group consisting of the first data and the second data may include sub-data of a text, sub-data of a video, and sub-data of a voice; in this case, the semantic comparison space enables it possible to calculate the similarity among the semantic representation obtained by mapping the sub-data of the text to the semantic comparison space, the semantic representation obtained by mapping the sub-data of the image to the semantic comparison space, and the semantic representation obtained by mapping the sub-data of the voice to the semantic comparison space.

At least one embodiment of the present disclosure also provides a data similarity determination device.

Figure 4:
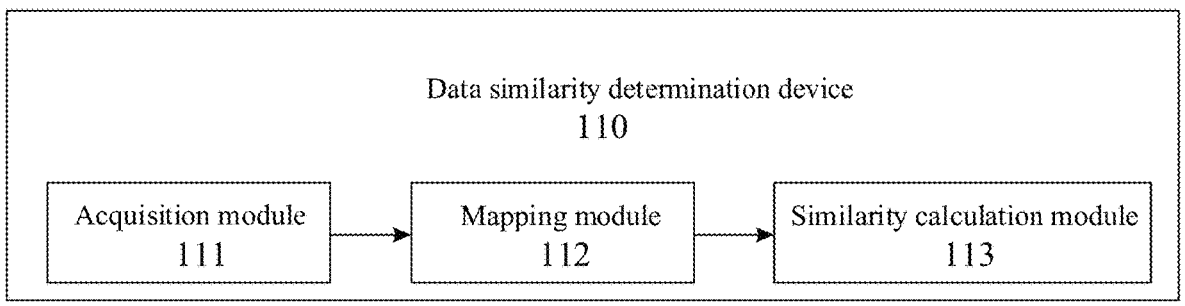
FIG. 4 is an exemplary block diagram of a data similarity determination device provided by at least one embodiment of the present disclosure.

FIG. 4 is an exemplary block diagram of a data similarity determination device 110 provided by at least one embodiment of the present disclosure. As shown in FIG. 4, the data similarity determination device 110 includes an acquisition module 111, a mapping module 112, and a similarity calculation module 113.

The acquisition module 111 is configured to acquire first data of a first object and second data of a second object. The first data includes first sub-data of a first modality or a second modality, and the second data includes second sub-data of the first modality or the second modality.

For example, the first object may be a given patient, and the second object may be a reference patient whose similarity with the given patient needs to be determined. For example, the first modality is different from the second modality. For example, the first modality is a text and the second modality is an image.

In an example, the first data further includes third sub-data of the second modality, and the second data further includes fourth sub-data of the second modality. The first object includes a first characteristic, the first sub-data includes a first sub-semantic describing the first characteristic, and the third sub-data includes a third sub-semantic describing the first characteristic; and the second object includes a second characteristic, the second sub-data includes a second sub-semantic describing the second characteristic, and the fourth sub-data includes a fourth sub-semantic describing the second characteristic.

The mapping module 112 is configured to map the first sub-data as a first semantic representation in the semantic comparison space and map the second sub-data as a second semantic representation in the semantic comparison space. The semantic comparison space at least enables a similarity between the semantic representation obtained by mapping the data of the first modality to the semantic comparison space and the semantic representation obtained by mapping the data of the second modality to the semantic comparison space to be computed.

For example, the mapping module 112 includes a first sub-mapping module and a second sub-mapping module; the first sub-mapping module is configured to map the sub-data of the first modality to the semantic comparison space, and the second sub-mapping module is configured to map the sub-data of the second modality to the semantic comparison space. For example, the first sub-mapping module can be implemented as a first neural network, and the second sub-mapping module can be implemented as a second neural network. For example, in the case where the first modality is the text and the second modality is the image, the first neural network can be a long-short-term memory network, word2vec, word2vect+LSTM, etc., and the second neural network can be a convolution neural network. Similarly, the embodiments of the present disclosure are not limited to this case, as long as the first neural network and the second neural network can respectively process the data of different modalities to obtain vectors in the same semantic space, and thus the similarity between the obtained different vectors can be calculated.

For example, in the case where the first data also includes third sub-data of the second modality and the second data also includes fourth sub-data of the second modality, the mapping module 112 is further configured to map the third sub-data as a third semantic representation in the semantic comparison space and map the fourth sub-data as a fourth semantic representation in the semantic comparison space. For example, the first sub-mapping module is configured to map the first sub-data as the first semantic representation of the semantic comparison space and map the second sub-data as the second semantic representation of the semantic comparison space. The second sub-mapping module is configured to map the third sub-data as the third semantic representation of the semantic comparison space and map the fourth sub-data as the fourth semantic representation of the semantic comparison space.

The similarity calculation module 113 is configured to calculate the similarity between the first data and the second data based on at least the first semantic representation and the second semantic representation.

For example, in the case where the first data also includes the third sub-data of the second modality and the second data also includes the fourth sub-data of the second modality, the similarity calculation module 113 is configured to obtain the similarity between the first data and the second data based on the first semantic representation, the second semantic representation, the third semantic representation, and the fourth semantic representation.

For example, the similarity calculation module 113 is configured to calculate the similarity between the first semantic representation and the fourth semantic representation, the similarity between the second semantic representation and the third semantic representation, the similarity between the first semantic representation and the second semantic representation, and the similarity between the third semantic representation and the fourth semantic representation. For example, the similarity between first data and the second data is equal to the sum of the similarity between the first semantic representation and the fourth semantic representation, the similarity between the second semantic representation and the third semantic representation, the similarity between the first semantic representation and the second semantic representation, and the similarity between the third semantic representation and the fourth semantic representation.

For example, for the calculation method of the similarity between the first data and the second data, reference may be made to the data similarity determination method provided by at least one embodiment of the present disclosure, and the similar descriptions will not be described in detail here.

For example, the acquisition module 111, the mapping module 112, the first sub-mapping module, the second sub-mapping module, and the similarity calculation module 113 can be implemented by software, firmware, hardware, or any combination of software, firmware, and hardware, for example, the hardware includes a Field Programmable Gate Array (FPGA) and the like.

At least one embodiment of the present disclosure also provides another data similarity determination device.

Figure 5:
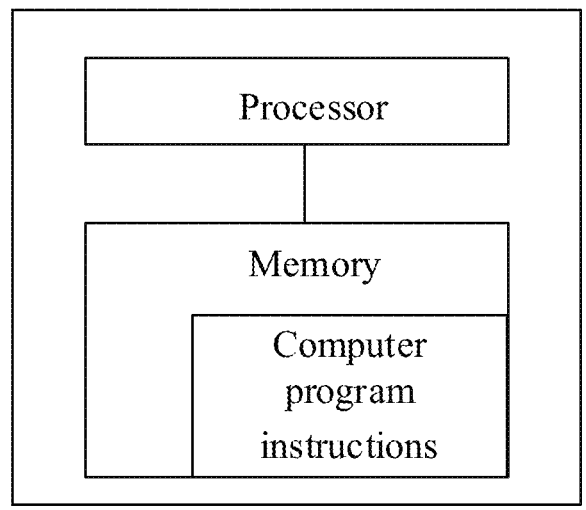
FIG. 5 is an exemplary block diagram of another data similarity determination device provided by at least one embodiment of the present disclosure.

FIG. 5 is an exemplary block diagram of another data similarity determination device provided by at least one embodiment of the present disclosure. As shown in FIG. 5, the data similarity determination device includes a processor and a memory. The memory stores computer program instructions which are suitable for execution by the processor, and in the case where the computer program instructions are executed by the processor, the processor executes any data similarity determination method provided by at least one embodiment of the present disclosure.

For example, the processor is a central processing unit (CPU), a graphics processor GPU, a tensor processor (TPU), or other forms of processing units with data processing capability and/or instruction execution capability. For example, the processor can be implemented as a general-purpose processor, and can also be a single chip microcomputer, a microprocessor, a digital signal processor, a dedicated image processing chip, or a field programmable logic array, etc. For example, the memory may include at least one selected from a group consisting of volatile memory and non-volatile memory, for example, the memory may include a read only memory (ROM), a hard disk, a flash memory, etc. Accordingly, the memory may be implemented as one or more computer program products, and the computer program product may include various forms of computer-readable storage media, one or more computer program instructions may be stored on the computer-readable storage medium. The processor may execute the program instructions to execute any data similarity determination method provided by at least one embodiment of the present disclosure. The memory can also store other various application programs and various data, for example, various data used and/or generated by the application programs, and the like.

The data similarity determination device provided by at least one embodiment of the present disclosure (the data similarity determination devices shown in FIGS. 4 and 5) can improve the accuracy of data similarity calculation results.

Figure 6:
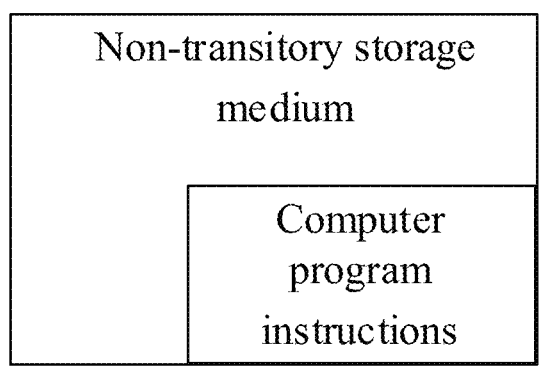
FIG. 6 is an exemplary block diagram of a non-transitory storage medium provided by at least one embodiment of the present disclosure.

At least one embodiment of the present disclosure also provides a non-transitory storage medium. FIG. 6 is an exemplary block diagram of a non-transitory storage medium provided by at least one embodiment of the present disclosure. As shown in FIG. 6, the non-transitory storage medium includes computer program instructions stored on the non-transitory storage medium, and in the case where the computer program instructions are executed by a processor, the computer executes any data similarity determination method provided by at least one embodiment of the present disclosure. For example, the non-transitory storage medium can include magnetic storage medium, optical storage medium, semiconductor storage medium, etc.; for example, the non-transitory storage medium may include a read only memory (ROM), a hard disk, a flash memory, and the like. For example, the non-transitory storage medium shown in FIG. 6 can be used in data similarity determination, and the accuracy of data similarity calculation results can be improved.

At least one embodiment of the present disclosure also provides a training method of a neural network for determining a data similarity.

Figure 7:
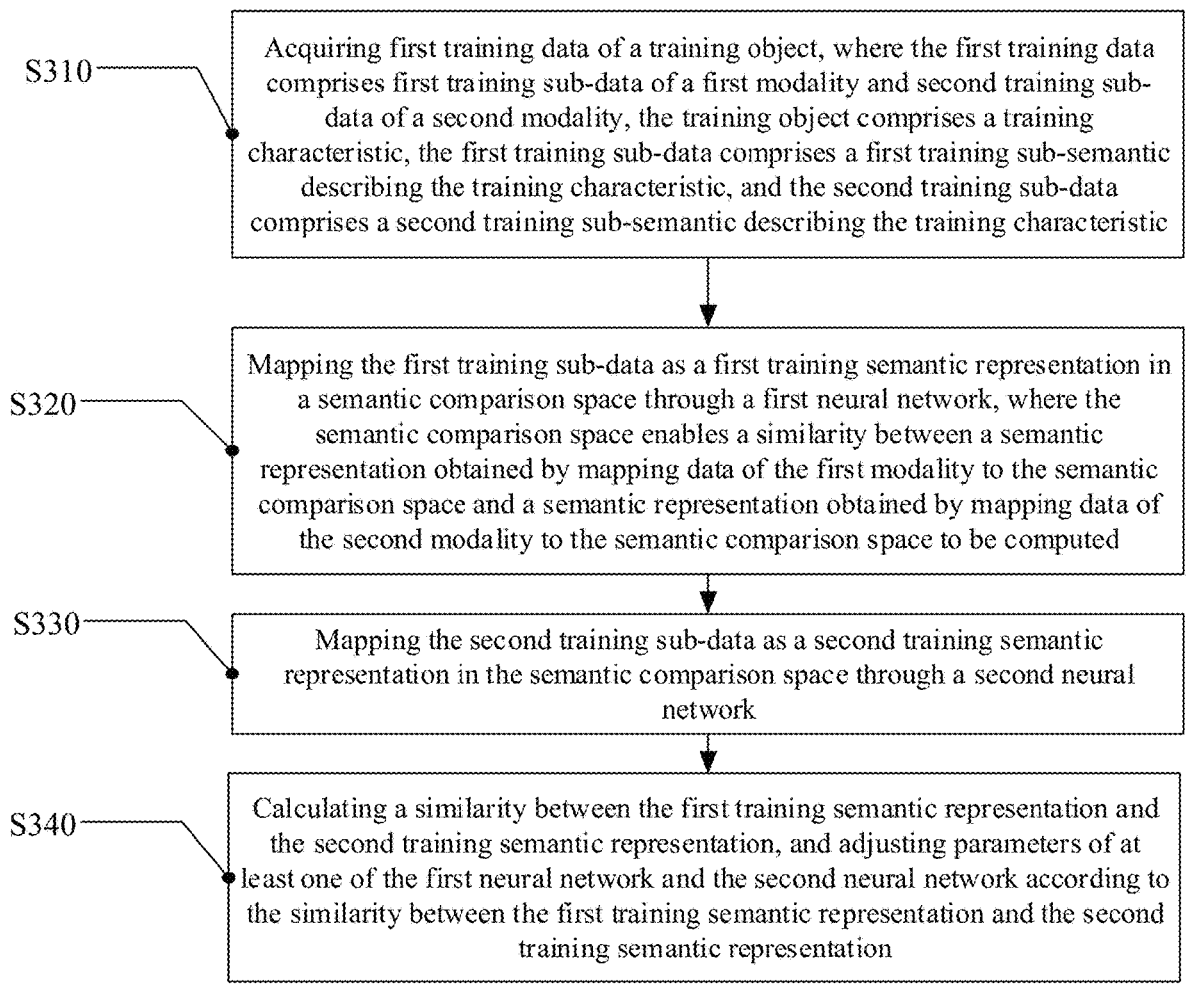
FIG. 7 is a flowchart of a training method of a neural network used for determining a data similarity provided by at least one embodiment of the present disclosure.

FIG. 7 is a flowchart of a training method of a neural network for determining a data similarity provided by at least one embodiment of the present disclosure. For example, the training method of the neural network for determining the data similarity shown in FIG. 7 can be used to train the first neural network and the second neural network.

As shown in FIG. 7, the training method of the neural network for determining the data similarity includes the following steps S310-S340.

S310: acquiring first training data of a training object, where the first training data comprises first training sub-data of a first modality and second training sub-data of a second modality, the training object comprises a training characteristic, the first training sub-data comprises a first training sub-semantic describing the training characteristic, and the second training sub-data comprises a second training sub-semantic describing the training characteristic.

S320: mapping the first training sub-data as a first training semantic representation in a semantic comparison space through a first neural network, where the semantic comparison space enables a similarity between a semantic representation obtained by mapping data of the first modality to the semantic comparison space and a semantic representation obtained by mapping data of the second modality to the semantic comparison space to be computed.

S330: mapping the second training sub-data as a second training semantic representation in the semantic comparison space through a second neural network.

S340: calculating a similarity between the first training semantic representation and the second training semantic representation, and adjusting parameters of at least one of the first neural network and the second neural network according to the similarity between the first training semantic representation and the second training semantic representation.

For example, the first modality is different from the second modality. For example, the first modality is a text and the second modality is an image. For another example, the first modality is an image and the second modality is a text. For example, in the case where the first modality is a text and the second modality is an image, the first neural network can be a long-short-term memory network, word2vec, word2vect+LSTM, etc., and the second neural network can be a convolution neural network. Similarly, the embodiments of the present disclosure are not limited to this case, as long as the first neural network and the second neural network can respectively process the data of different modalities to obtain vectors in the same semantic space, and therefore, the similarity between the obtained different vectors can be calculated.

For example, both the first training semantic representation and the second training semantic representation are expressed as vectors, that is, both the first training semantic representation and the second training semantic representation are vectors in the semantic comparison space. For example, the dimension of the vector corresponding to the first training semantic representation is the same as the dimension of the vector corresponding to the second training semantic representation. For example, the training characteristics refer to the characteristics of the first neural network and the second neural network to be trained. The trained first neural network and the trained second neural network can map the sub-data (for example, the sub-data of different modalities) of the first object corresponding to the training characteristics to the semantic comparison space, respectively, and enable the dimensions of the vectors corresponding to the obtained semantic representations to be the same and enable the values of the vectors corresponding to the semantic representations in each dimension to be similar, so that calculation and comparison can be performed. For example, when training the first neural network and the second neural network, training can be performed for one or more training characteristics.

For example, the cosine similarity can be used to calculate the similarity between the first training semantic representation and the second training semantic representation. For example, the calculation method of the cosine similarity can refer to the data similarity determination method provided by at least one embodiment of the present disclosure, and the similar descriptions will not be described in detail here.

For example, adjusting parameters of at least one selected from a group consisting of the first neural network and the second neural network according to the similarity between the first training semantic representation and the second training semantic representation includes: calculating a loss function based on the similarity between the first training semantic representation and the second training semantic representation; and minimizing the loss function by adjusting the parameters of at least one selected from a group consisting of the first neural network and the second neural network.

For example, the first training data of M (e.g., M is a positive integer greater than 1) training objects (e.g., M past patients) can be used to train the first neural network and the second neural network, so as to determine the related parameters of the first neural network and the related parameters of the second neural network. Therefore, the first neural network and the second neural network, which are obtained by training using the first training data of the M training objects and the training method of the neural network for determining the data similarity, can make the sub-data of different modalities of the same object (the same first object) keep semantic consistency after being mapped to the semantic comparison space.

For example, in step S310, the first training data of the M training objects may be acquired, in step S320, the first training sub-data of the M training objects can be respectively converted into M first training semantic representations. In the step S330, the second training sub-data of the M training objects can be respectively converted into M second training semantic representations. In step S340, the similarities of the first training semantic representations and the second training semantic representations of the M training objects can be calculated respectively, and the loss function (or error function) can be calculated based on the similarities of the first training semantic representations and the second training semantic representations of the M training objects, and then the loss function can be minimized by adjusting the parameters of at least one of the first neural network and the second neural network respectively (for example, adjusting the parameters of the first neural network and the second neural network).

For example, the loss function 1 can be obtained by adopting the following expression:

$$l = \frac{1}{2}\sum_{i=1}^{M}(1 - sim_2(trt_i, trg_i))^2$$
$$= \frac{1}{2}\sum_{i=1}^{M}(1 - \cos(NN1(trt_i), NN2(trg_i)))^2,$$

here $trt_i$ is first training sub-data of an i-th training object, and $trg_i$ is second training sub-data of the i-th training object, $sim_2(trt_i, trg_i)$ is the similarity between the first training sub-data of the i-th training object and the second training sub-data of the i-th training object, NN1 refers to mapping a corresponding training sub-data by using the first neural network, NN2 refers to mapping a corresponding training sub-data by using the second neural network, $NN1(trt_i)$ is a first training semantic representation of the i-th training object, and $NN2(trg_i)$ is a second training semantic representation of the i-th training object.

For example, minimizing the loss function by adjusting the parameters of at least one selected from a group consisting of the first neural network and the second neural network includes adjusting the parameters of at least one selected from a group consisting of the first neural network and the second neural network based on a gradient descent method (e.g., a stochastic gradient descent method) or other applicable methods (e.g., a genetic algorithm, a back propagation algorithm). For example, adjusting the parameters of at least one selected from a group consisting of the first neural network and the second neural network includes adjusting the parameters of at least one selected from a group consisting of the first neural network and the second neural network many times. For example, adjusting the parameters of at least one selected from a group consisting of the first neural network and the second neural network many times can enable the loss function to gradually decrease. For example, in the case where the loss function is less than a loss function threshold (e.g., 0.01) or the number of times of the parameter adjustment is greater than a threshold (e.g., 10,000 times) of the number of adjustment times, the loss function is considered to be minimized.

For example, the gradient descent method is used to find the local minimum of a function. For example, the adjustment of the parameters of at least one of the first neural network and the second neural network in order to minimize the loss function (error function) can be regarded as aiming to finding a movement of the minimum point on an error plane.

For example, in the gradient descent algorithm, the learning rate determines the degree of modifying the weights in the learning process; in an initial stage, a higher rate can be set to quickly explore the error plane and approach an optimal solution (the minimum value of the plane), and then in a later stage, the rate can be reduced to approach the optimal solution as much as possible. The higher the learning rate means the faster the learning, but the greater the risk that the neural network converges outside the optimal solution. Moment can be used as a damping parameter to reduce the oscillation and help to achieve convergence. Generally speaking, the smaller the moment, the better the adaptability of the network to the environment. The moment tends to keep the weights in the same changing direction (increase or decrease), and the moment limits the oscillation caused by irregularities in learning examples.

For example, the learning rate of the neural network controls the moving speed, and the moment of the neural network controls the direction change on the error plane; by continuously moving in the same direction for many times on the error plane, it is possible to avoid falling to the local minimum of the loss function (error function), but to reach the global minimum of the loss function (error function) through the local minimum. For example, in the initial stage of training the neural network, it can quickly move in all directions, and at last, the moving speed and the frequency of direction change can be reduced. For example, the specific method of adjusting the parameters of the neural network based on the gradient descent method (e.g., the stochastic gradient descent method) can refer to related technologies, and will not be described in detail here.

For example, by adjusting the parameters of at least one of the first neural network and the second neural network to minimize the loss function (for example, enabling the loss function to be equal to zero or close to zero), the similarity between the first training semantic representation and the second training semantic representation of the training object can be maximized, thereby ensuring that the similarity of the sub-data of different modalities of the same training object is maximum, that is, the first neural network and the second neural network, which are trained by the first training data of the M training objects and the training method of the neural network for determining the data similarity, can maintain the semantic consistency of the sub-data of different modalities (for example, the sub-data of different modalities corresponding to the same first object) after being mapping to the semantic comparison space in the process of performing the data similarity determination method.

For example, according to actual application requirements, the training method of the neural network for determining the data similarity further includes the following step S350.

S350: performing data preprocessing on original data before acquiring the first training data of the training object.

For example, the original data includes data of N (N is a positive integer greater than or equal to M) objects to be selected, and performing data preprocessing on original data includes selecting objects to be selected, which meet the following requirements, among the N objects to be selected as M training objects: that is, the objects to be selected whose first training data includes both the first training sub-data of the first modality and the second training sub-data of the second modality.

For example, the N objects to be selected can be sorted, and the objects to be selected whose first training data includes both the first training sub-data of the first modality and the second training sub-data of the second modality are arranged in front of the queue. In this case, when acquiring the first training data of the training object, the first M objects to be selected in the original data can be directly selected as the M training objects, thereby simplifying step S310.

For example, the data similarity determination method may be executed in the order of step S310, step S320, step S330, and step S340, but the embodiments of the present disclosure are not limited thereto. For another example, the data similarity determination method may be executed in the order of step S310, step S320+step S330 (that is, step S320 and step S330 are executed simultaneously), and step S340.

At least one embodiment of the present disclosure also provides a training device of a neural network used for determining a data similarity.

Figure 8:
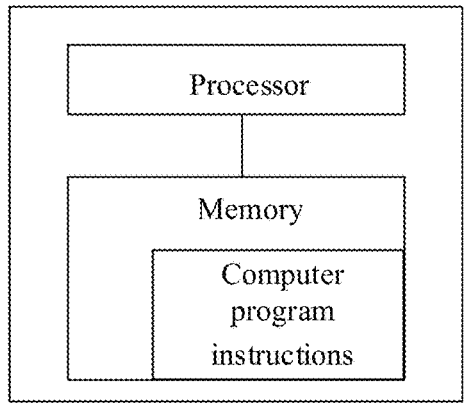
FIG. 8 is an exemplary block diagram of a training device of a neural network used for determining a data similarity provided by at least one embodiment of the present disclosure.

FIG. 8 is an exemplary block diagram of a training device of a neural network used for determining a data similarity provided by at least one embodiment of the present disclosure. For example, the training device of the neural network used for determining the data similarity shown in FIG. 8 can be used to train the first neural network and the second neural network.

As shown in FIG. 8, the training device of the neural network used for determining the data similarity includes a processor and a memory. The memory has stored the computer program instructions which are executed by the processor, in the case where the computer program instructions are executed by the processor, the processor executes any of the training methods provided by at least one embodiment of the present disclosure. For example, the specific implementations of the processor and the memory shown in FIG. 8 can refer to the processor and the memory shown in FIG. 5, and the similar descriptions will not be described in detail here.

At least one embodiment of the present disclosure also provides another non-transitory storage medium, the non-transitory storage medium includes computer program instructions stored thereon, and in the case where the computer program instructions are executed by a processor, a computer executes any of the training methods provided by at least one embodiment of the present disclosure. For example, the non-transitory storage medium can include magnetic storage medium, optical storage medium, semiconductor storage medium, etc.; for example, the non-transitory storage medium may include a read only memory (ROM), a hard disk, a flash memory, and the like. For example, another non-transitory storage medium provided by at least one embodiment of the present disclosure can be used to train the first neural network and the second neural network.

At least one embodiment of the present disclosure also provides a similar object search method.

Figure 9:
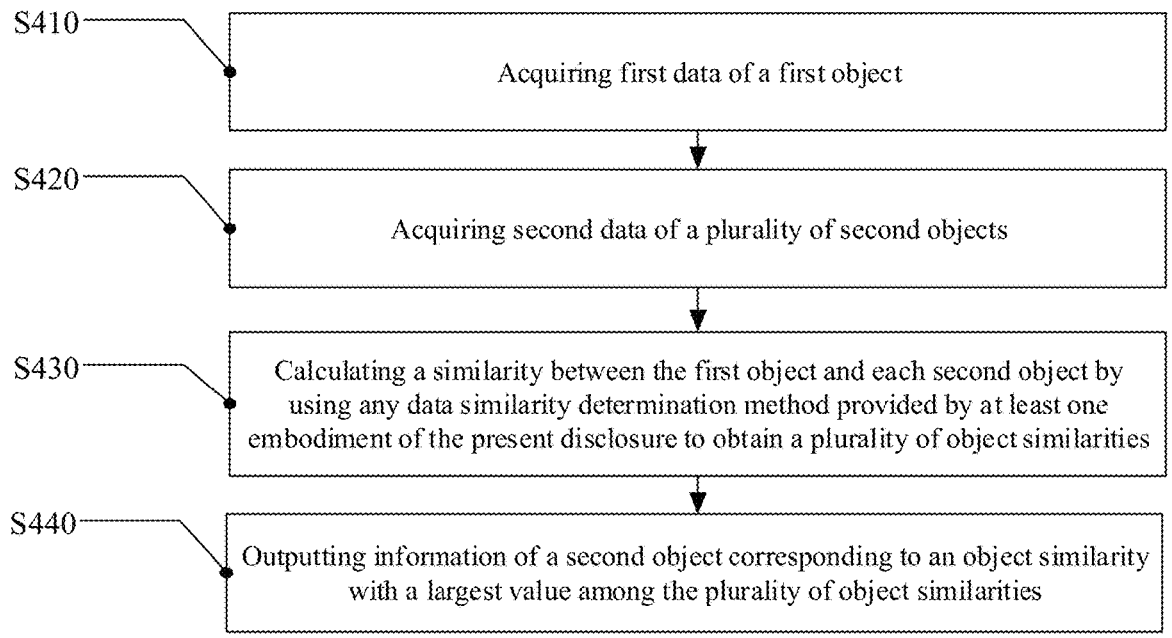
FIG. 9 is a flowchart of a similar object search method provided by at least one embodiment of the present disclosure.

FIG. 9 is a flowchart of a similar object search method provided by at least one embodiment of the present disclosure. As shown in FIG. 9, the similar object search method includes the following steps S410-S440.

S410: acquiring first data of a first object.

S420: acquiring second data of a plurality of second objects.

S430: calculating a similarity between the first object and each second object by using any data similarity determination method provided by at least one embodiment of the present disclosure to obtain a plurality of object similarities.

S440: outputting information of a second object corresponding to an object similarity with a largest value among the plurality of object similarities.

For example, the first data of the first object can be acquired through the human-computer interaction interface. For example, a first user is a given patient, i.e., a patient currently seeking treatment. For example, the first data includes first sub-data of the first modality or the second modality. For example, the first data also includes third sub-data of the second modality or the first modality. For example, the first data includes the first sub-data of the first modality and the third sub-data of the second modality; for another example, the first data includes the first sub-data of the second modality and the third sub-data of the first modality. For example, the first modality is a text and the second modality is an image.

For example, the second data of the plurality of second objects can be acquired from an object database. For example, the object database (e.g., a past patient database) stores data of a plurality of objects. For example, the plurality of second objects are a plurality of past patients. For example, the data of each of the plurality of objects includes at least one (e.g., all) of sub-data of the first modality and sub-data of the second modality. For example, the information of the second object (i.e., a similar object) corresponding to the object similarity with the largest value among the plurality of object similarities can be output through the human-computer interaction interface (e.g., a information display region of the human-computer interaction interface).

For example, the specific content of the information of the similar object displayed in the information display region can be set based on the actual requirements of users. For example, the information of the similar object displayed in the information display region may include summary information or important information; for example, the information display region can also display relevant information according to the requirements of the users. For example, the above-mentioned summary information includes the object similarity, important information that users care about (for example, the text information and image information about whether there are nodules in the lungs, diagnosis and treatment scheme), and so on. For example, the relevant information includes information related to the above important information (e.g., the treatment cost, the length of hospital stay, etc.).

For example, in step S440, outputting the information of the second object corresponding to the object similarity with the largest value among the plurality of object similarities includes: outputting the information of the second object corresponding to a first number of object similarities with the largest value among the plurality of object similarities. For example, the first number (K) is a positive integer and greater than 1. For example, the first number (K) may be set based on the requirements of the uses, for example, K=5 or 10. For example, by outputting the information of the second objects corresponding to the first number of object similarities with the largest value among the plurality of object similarities, the user can refer to the information of the first number of second objects at the same time and manually confirm the object closest to the first object among the first number of second objects, thereby improving the applicability of the similar object search method provided by at least one embodiment of the present disclosure.

For example, the similar object search method can be executed in the order of step S410, step S420, step S430, and step S440, but the embodiments of the present disclosure are not limited to this case. For another example, the similar object search method can be executed in the order of step S410+step S420 (that is, step S410 and step S420 are executed simultaneously), step S430, and step S440.

For example, according to actual application requirements, the similar object search method further includes the following step S450.

S450: after acquiring the plurality of object similarities and before outputting the information of the second object corresponding to the object similarity with the largest value among the plurality of object similarities, sorting the plurality of second objects based on the plurality of object similarities.

For example, sorting the plurality of second objects based on the plurality of object similarities includes sorting the plurality of second objects using a sequential sorting method based on the plurality of object similarities; in this case, when outputting the information of the second object corresponding to the object similarity with the largest value among the plurality of object similarities, the information of the second object located at the first position of the sequence (or the first K second objects in the sequence) can be directly output, thereby simplifying step S440.

For example, by using any data similarity determination method provided by at least one embodiment of the present disclosure to calculate the similarity between the first object and each second object, the accuracy of the data similarity calculation result can be improved, and therefore, the searching performance of the similar object search method provided by at least one embodiment of the present disclosure can be improved (for example, more similar objects can be found).

At least one embodiment of the present disclosure also provides a similar object search device, which comprises any data similarity determination device provided by at least one embodiment of the present disclosure.

Figure 10:
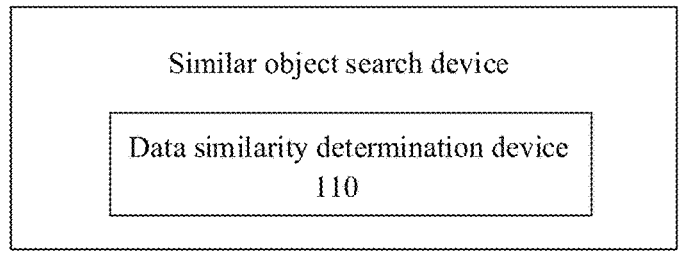
FIG. 10 is an exemplary block diagram of a similar object search device provided by at least one embodiment of the present disclosure.

FIG. 10 is an exemplary block diagram of a similar object search device provided by at least one embodiment of the present disclosure. As shown in FIG. 10, the similar object search device includes any data similarity determination device 110 provided by at least one embodiment of the present disclosure.

The similar object search device shown in FIG. 10 will be exemplarily described with reference to FIGS. 11 and 12.

Figure 11:
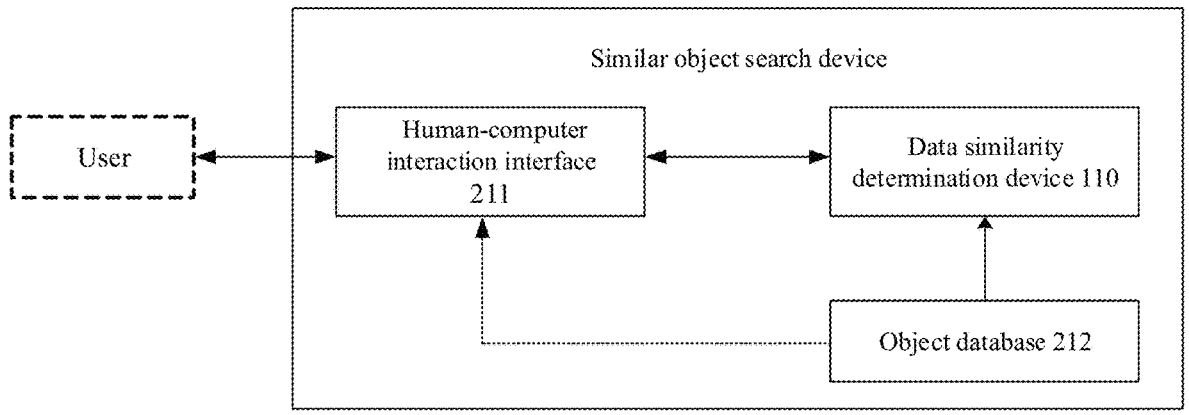
FIG. 11 is an exemplary block diagram of an example of the similar object search device shown in FIG. 10.

FIG. 11 is an exemplary block diagram of an example of the similar object search device shown in FIG. 10. As shown in FIG. 11, the similar object search device includes any data similarity determination device 110 provided by at least one embodiment of the present disclosure, a human-computer interaction interface 211, and an object database 212. For example, the similar object search device shown in FIG. 11 may be a dedicated device dedicated to search the similar object.

The human-computer interaction interface 211 is used to implement the interaction between an operator (e.g., a medical worker, a user) and a computer, and can be implemented as a text interaction interface, an image interaction interface, etc. For example, the human-computer interaction interface 211 can be implemented by various appropriate types of input and output devices, such as a display, a touch panel, a mouse, a keyboard, a touch ball, etc.

For example, the human-computer interaction interface 211 is configured to receive first data of a first object and provide the first data to the data similarity determination device 110. The object database 212 stores data of a plurality of objects and provides the data of at least part of the objects to the data similarity determination device 110 as second data of a plurality of second objects. The data similarity determination device 110 is configured to provide the similarities between the first object and respective second objects as a plurality of object similarities; the human-computer interaction interface 211 is also configured to output the information of the second object corresponding to the object similarity with the largest value among the plurality of object similarities.

For example, the human-computer interaction interface 211 includes an information input region, an operator (e.g., the medical worker or the user) inputs the first data of the first object through the information input region, so that the human-computer interaction interface 211 can receive the first data of the first object. For example, the first object is a given patient, that is, a patient currently seeking treatment. For example, the first data includes first sub-data of the first modality or the second modality. For example, the first data also includes third sub-data of the second modality or the first modality. For example, the first modality is a text and the second modality is an image.

For example, the object database 212 stores the data of the plurality of objects, the plurality of objects are a plurality of past patients. For example, the data of each of the plurality of objects includes at least one selected from a group consisting of sub-data of the first modality and sub-data of the second modality.

For example, the object database (patient database) will be described below by taking the case that the plurality of objects are the plurality of patients as an example. For example, (t, g) can be used to represent the patient's information, where t represents the medical record data of the patient and g represents the image data of the patient. t or g can be empty, indicating that the patient lacks this part of information. For example, patients with common influenza may only have medical records without image data, and g is empty in this case. Assuming that the patient database contains N patient information, the patient database can be denoted as S={(t1, g1), (t2, g2), . . . , (tN, gN)}.

For example, the object database 212 is a device having a storage function. The object database 212 is mainly used for storing the data of the plurality of objects. The object database 212 may be local or remote. The object database 212 may include various memories, such as random access memory (RAM), read only memory (ROM), and the like.

For example, after or at the same time when the data similarity determination device 110 receives the first data of the first object, the data similarity determination device 110 acquires data of at least part of the objects from the object database 212 as the second data of the plurality of second objects. For example, for the specific implementation of providing the similarities between the first object and respective second objects as the plurality of object similarities by the data similarity determination device 110 shown in FIG. 11 provided by at least one embodiment of the present disclosure, reference may be made to the data similarity determination device 110 or the data similarity determination method provided by at least one embodiment of the present disclosure, and the similar descriptions will not be described in detail here.

For example, the specific method in which the data similarity determination device 110 obtains data of at least part of objects from the object database 212 can be set according to actual application requirements. For example, the data similarity determination device 110 may acquire data of a predetermined number of objects from the object database 212 at one time; for another example, the data similarity determination device 110 may also acquire the data of one object from the object database 212 at a time, until the data of the predetermined number of objects are acquired or the objects meeting the requirements are found.

For example, the human-computer interaction interface 211 also includes an information display region; the human-computer interaction interface 211 is also configured to output the information of the second object (i.e., the similar object) corresponding to the object similarity with the largest value among the plurality of object similarities in the information display region, so as to serve as the similar object for the user's reference. For example, outputting the information of the second object corresponding to the object similarity with the largest value among the plurality of object similarities includes outputting the information of the second object corresponding to the first number of object similarities with the largest value among the plurality of object similarities. For example, for the specific contents of the information of similar objects displayed in the information display region, reference may be made to the similar object search method provided by at least one embodiment of the present disclosure, and the repeated parts will not be described in detail here.

For example, the specific method in which the human-computer interaction interface 211 obtains and outputs the information of the second object corresponding to the object similarity with the largest value among the plurality of object similarities can be set according to the actual application requirements, the embodiments of the present disclosure are not specifically limited to this case. For example, the human-computer interaction interface 211 may receive all the information of the second object corresponding to the object similarity with the largest value among the plurality of object similarities from the data similarity determination device 110, and display only the information required by the user according to the user settings. For another example, the human-computer interaction interface 211 may also receive an identifier and the object similarity of the second object corresponding to the object similarity with the largest value among the plurality of object similarities from the data similarity determination device 110, and then obtain the information required by the user from the object database 212 based on the identifier of the second object, and then the information required by the user and the object similarity is displayed in the display region; for example, when the user needs to view the further information of the object, the human-computer interaction interface 211 obtains the new information required by the user from the object database again based on the identifier of the second object. In this case, the overall communication volume of the similar object search device shown in FIG. 11 can be reduced.

For example, because the first data of the first object and the second data of the second object are both mapped to the semantic comparison space where a similarity between semantic representations corresponding to sub-data of different modalities can be calculated, the similar object search device shown in FIG. 11 can utilize the information complementarity of the data of different modalities and/or the characteristics of verifying and rechecking the data of different modalities each other, so that the similar object search device shown in FIG. 11 can improve the performance of searching the similar objects.

Figure 12:
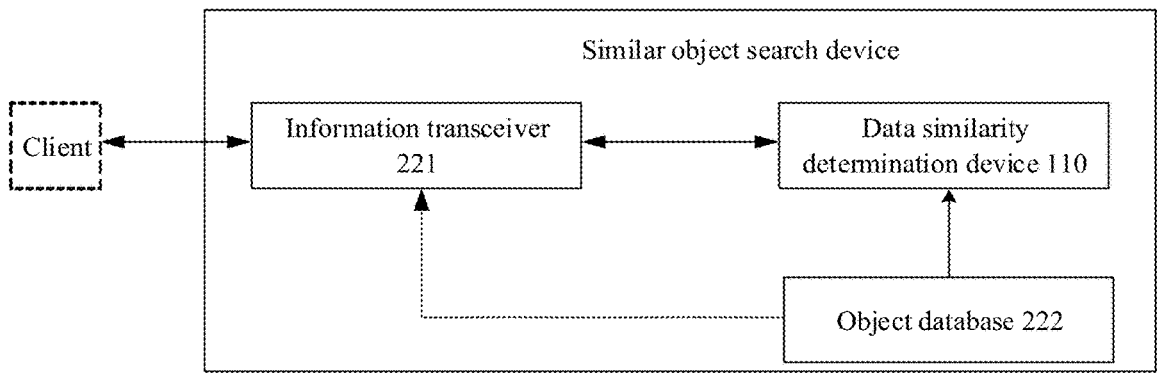
FIG. 12 is an exemplary block diagram of another example of the similar object search device shown in FIG. 10.

FIG. 12 is an exemplary block diagram of another example of the similar object search device shown in FIG. 10. As shown in FIG. 12, the similar object search device includes an information transceiver 221, an object database 222, and any data similarity determination device 110 provided by at least one embodiment of the present disclosure. For example, the function of the similar object search device shown in FIG. 12 can be achieved by a server, the server can be a single server or a server group, and respective servers in the server group are connected through a wired network or a wireless network. The wired network can, for example, communicate by twisted pair, coaxial cable, or optical fiber transmission etc., and the wireless network can, for example, communicate by 3G/4G/5G mobile communication network, Bluetooth, Zigbee, or WiFi, etc. The present disclosure does not limit the type and function of the network here. The server group can be centralized, such as a data center, or distributed. The servers can be local or remote. For example, the server can be a general-purpose server or a special-purpose server, and can be a virtual server, or a cloud server, or the like.

For example, the information transceiver 221 may include a modem, a network adapter, a Bluetooth transceiver unit, or an infrared transceiver unit, etc. For example, the information transceiver 221 may also perform encoding, decoding, and other operations on the transmitted or received information.

For example, the information transceiver 221 shown in FIG. 12 is configured to receive the first data of the first object from a client and provide the first data to the data similarity determination device 110. For example, the information transceiver 221 can transmit and receive information through, for example, a network or other technologies. For example, the network may be a single network or a combination of at least two different networks. For example, the network may include, but is not limited to, one or a combination of several of a group consisting of a local area network, a wide area network, a public network, a private network, the Internet, a mobile communication network, etc., other technologies may include, for example, Bluetooth communication, infrared communication, and the like.

For example, the object database 222 stores the data of the plurality of objects, the plurality of objects are the plurality of past patients. For example, the specific implementation of the object database 222 can refer to the object database 212 shown in FIG. 11, and the repeated parts will not be described in detail here.

For example, after the data similarity determination device 110 shown in FIG. 12 receives the first data of the first object, the data similarity determination device 110 acquires data of at least part of the objects from the object database 222 as the second data of the plurality of second objects. For example, the data similarity determination device 110 shown in FIG. 12 is configured to provide the similarities between the first object and respective second objects, respectively, as the plurality of object similarities. For example, the specific implementation of providing the similarities between the first object and respective second objects, respectively, as the plurality of object similarities by the data similarity determination device 110 shown in FIG. 12 can refer to the data similarity determination device 110 or the data similarity determination method provided by at least one embodiment of the present disclosure, and the repeated parts will not be described in detail here.

For example, the information transceiver 221 is further configured to receive the information of the second object corresponding to the object similarity with the largest value among the plurality of object similarities, and provide the information of the second object corresponding to the object similarity with the largest value among the plurality of object similarities to the client. For example, providing the information of the second object corresponding to the object similarity with the largest value among the plurality of object similarities includes providing the information of the second objects corresponding to the first number of object similarities with the largest value among the plurality of object similarities.

For example, the specific method in which the information transceiver 221 receives and provides the information of the second object corresponding to the object similarity with the largest value among the plurality of object similarities can be set according to the actual application requirements, the embodiments of the present disclosure are not specifically limited to this case. For example, the information transceiver 221 may receive all the information of the second object corresponding to the object similarity with the largest value among the plurality of object similarities from the data similarity determination device 110, and provide the above-mentioned all the information of the second object corresponding to the object similarity with the largest value among the plurality of object similarities to the client, and the client only displays the information required by the user according to the user settings. For another example, the information transceiver 221 may also receive the identifier and the object similarity of the second object corresponding to the object similarity with the largest value among the plurality of object similarities from the data similarity determination device 110, then obtain the information currently needed by the user from the object database 222 based on the identifier of the second object, and provide the information currently needed by the user and the object similarity to the client. For example, when the user needs to view further information of the object, the information transceiver 221 acquires new information required by the user from the object database 222 again based on the identifier of the second object; and in this case, the overall communication volume of the similar object search device shown in FIG. 12 can be reduced.

At least one embodiment of the present disclosure also provides a similar object search device, which comprises a human-computer interaction interface and an information transceiver. The human-computer interaction interface is configured to receive first data of a first object and provide the first data to a server; the information transceiver is further configured to receive second data of a first number of second objects, which have the greatest similarity to the first data of the first object, from the server; the similarity between the first object and each second object is determined by any data similarity determination device provided by at least one embodiment of the present disclosure.

Figure 13:
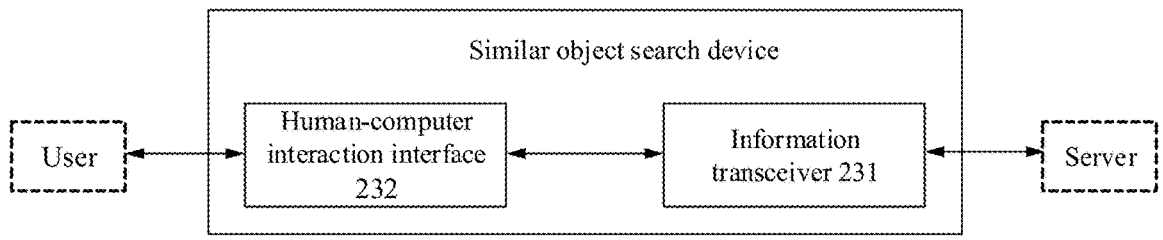
FIG. 13 is an exemplary block diagram of another similar object search device provided by at least one embodiment of the present disclosure.

FIG. 13 is an exemplary block diagram of another similar object search device provided by at least one embodiment of the present disclosure. As shown in FIG. 13, the similar object search device includes a human-computer interaction interface 232 and an information transceiver 231. For example, the similar object search device shown in FIG. 13 can be an integral part of other electronic devices (e.g., mobile phones, tablet computers, notebook computers, etc.). For another example, the similar object search device shown in FIG. 13 may also be a dedicated device dedicated to search the similar object.

For example, the human-computer interaction interface 232 is configured to receive the first data of the first object and provide the first data to the information transceiver 231. For example, the specific implementation method of the human-computer interaction interface 232 can refer to the human-computer interaction interface shown in FIG. 11, and the repeated parts will not be described in detail here.

For example, the information transceiver 231 is configured to provide the first data to the server; the information transceiver 231 is further configured to receive the second data of the first number of second objects, which have the greatest similarity to the first data of the first object, from the server, and provide the second data of the first number of second objects, which have the greatest similarity to the first data of the first object, to the human-computer interaction interface 232. For example, providing the information of the second object corresponding to the object similarity with the largest value among the plurality of object similarities includes providing the information of the second objects corresponding to the first number of object similarities with the largest value among the plurality of object similarities.

For example, the information transceiver 231 can transmit and receive the information through a network or other technologies, for example, the network can be a single network or a combination of at least two different networks. For example, the network may include but is not limited to, one or a combination of several of a group consisting of a local area network, a wide area network, a public network, a private network, the Internet, a mobile communication network, and the like. For example, the information transceiver 231 may include a modem, a network adapter, a Bluetooth transceiver unit, or an infrared transceiver unit, and the like. For example, the information transceiver 231 may also perform encoding, decoding, and other operations on the transmitted or received information.

For example, the similarity between the first object and each second object is determined by any data similarity determination device provided by at least one embodiment of the present disclosure. For example, the specific calculation method of obtaining the similarity between the first object and each second object by the similar object search device shown in FIG. 13 can refer to the data similarity determination device or the data similarity determination method provided by at least one embodiment of the present disclosure, and the repeated parts will not be described in detail here.

Figure 14:
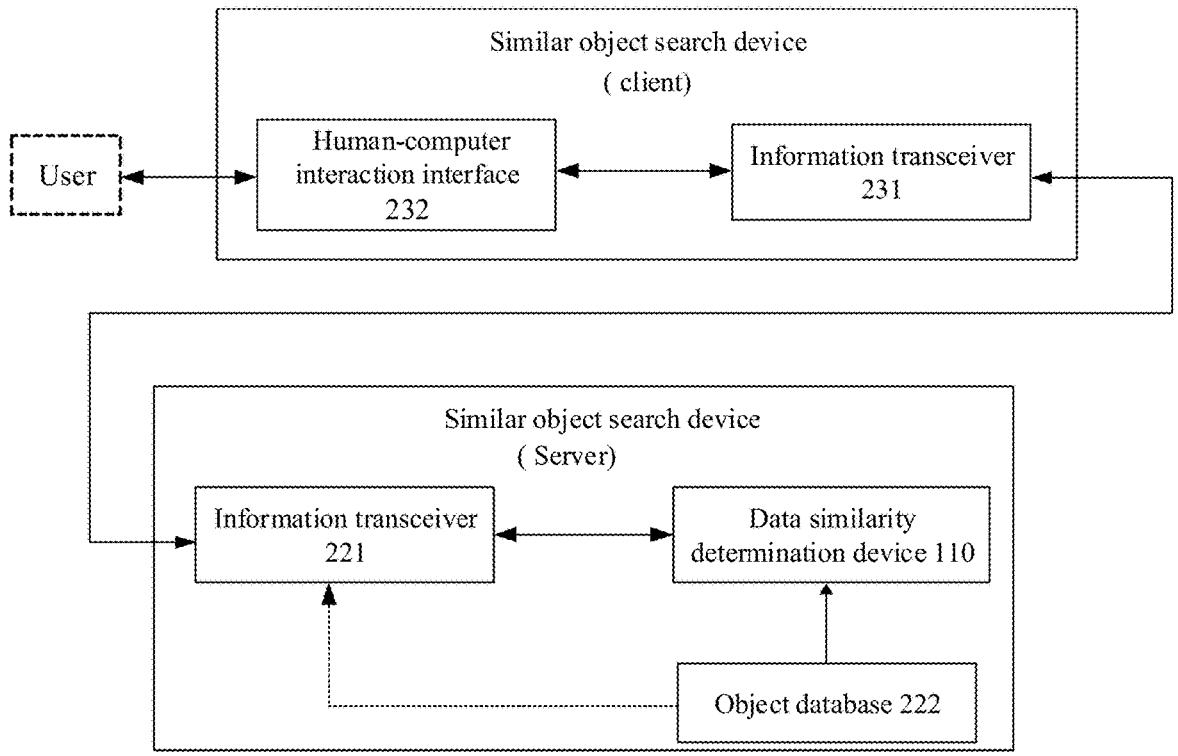
FIG. 14 is a schematic diagram of a similar object search system provided by at least one embodiment of the present disclosure.

For example, the similar object search device shown in FIG. 12 that serves as a server and the similar object search device shown in FIG. 13 that serves as a client can cooperate with each other to form a similar object search system as shown in FIG. 14, and the client and the server can be located at the same place or different places.

Figure 15:
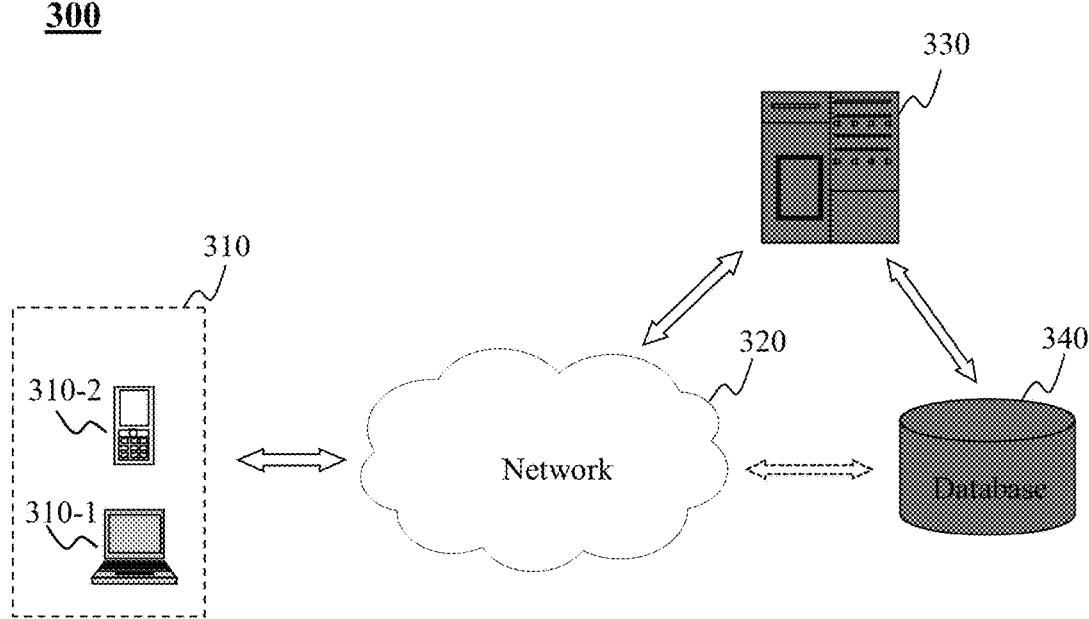
FIG. 15 is an exemplary scenario diagram of a similar object search system provided by at least one embodiment of the present disclosure.

FIG. 15 shows an exemplary scenario diagram of a similar object search system provided by at least one embodiment of the present disclosure. As shown in FIG. 15, the similar object search system 300 may include a user terminal 310, a network 320, a server 330, and a database 340.

For example, the user terminal 310 may be a computer 310-1 or a portable terminal 310-2 shown in FIG. 15. It can be understood that the user terminal can also be any other type of electronic equipment capable of receiving, processing, and displaying data, the user terminal can include but is not limited to desktop computers, notebook computers, tablet computers, smart home devices, wearable devices, vehicle-mounted electronic devices, monitoring devices, medical electronic devices, and the like.

The user terminal provided according to at least one embodiment of the present disclosure may be used to receive first data of a first object. For example, the user terminal may receive the first data of the first object via a human-computer interaction interface on the user terminal. For another example, the user terminal may also receive the first data of the first object from the server via the network. For another example, the user terminal may also receive the first data of the first object via a network or directly from a data acquisition device such as a medical acquisition device.

In some embodiments, the data similarity determination method provided by at least one embodiment of the present disclosure may be performed by a processing unit of the user terminal. In this case, the user terminal has a database storing a plurality of objects (i.e., an object database), or communicates with the object database via a network or other technologies to acquire second data of a plurality of second objects. In some implementations, the user terminal can use the built-in application program of the user terminal to execute the data similarity determination method provided by at least one embodiment of the present disclosure. In other implementations, the user terminal can execute the data similarity determination method provided by at least one embodiment of the present disclosure by calling an application program stored outside the user terminal.

In other embodiments, the user terminal transmits the received first data to the server 330 via the network 320 or other technologies, and the server 330 obtains the second data of the plurality of second objects from the object database, and executes the data similarity determination method provided by at least one embodiment of the present disclosure to obtain the similarity between the first data of the first object and the second data of the second object, then, the user terminal can receive and display the similarity between the first data of the first object and the second data of the second object provided by the server 330 and the information of similar objects determined based on the above similarity. In some implementations, the server 330 may use the built-in application program of the server to execute the data similarity determination method provided by at least one embodiment of the present disclosure.

In other implementations, the server 330 may execute the data similarity determination method provided by at least one embodiment of the present disclosure by calling an application program stored outside the server.

For example, the specific implementations of the network 320, other technologies, and the server 330 can refer to the network, other technologies, and the server of the above embodiments, and the repeated parts will not be described in detail here.

The database 340 may include an object database provided by at least one embodiment of the present disclosure to store the data of the plurality of objects. For example, the database 330 can also be used to store various data, which is used by, generated by, and output from the user terminal 310 and the server 330 during operation. The database 340 can be interconnected with or communicate with the server 330 or a part of the server 330 via the network 320, directly interconnected with or communicate with the server 330, or interconnected with or communicate with the server 330 via a combination of the above two methods.

In some embodiments, the database 340 may be an independent device. In other embodiments, the database 340 may also be integrated in at least one of the user terminal 310 and the server 340. For example, the database 340 can be disposed on the user terminal 310 or on the server 340. For another example, the database 340 may also be distributed, one part of the database 340 is disposed on the user terminal 310, and the other part of the database 340 is disposed on the server 340.

Figure 16:
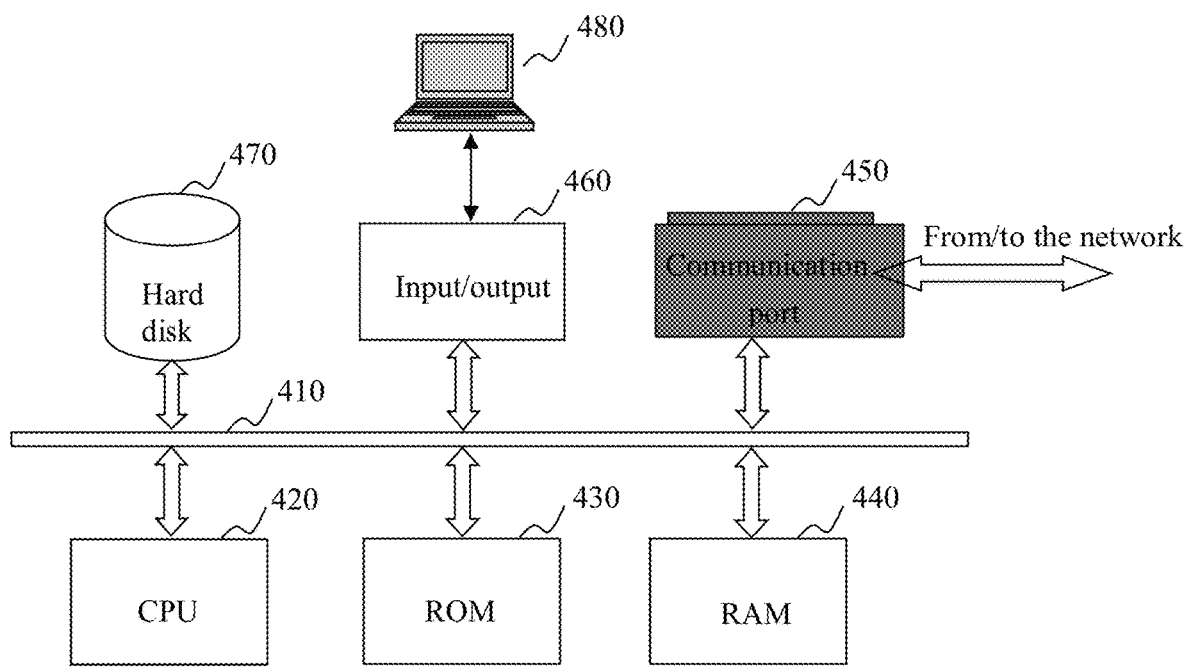
FIG. 16 is a schematic diagram of a computing device provided by at least one embodiment of the present disclosure.

The method, device, or system according to the embodiments of the present application can also be implemented by means of the architecture of a computing device 400 shown in FIG. 16.

FIG. 16 shows a schematic diagram of the architecture of the computing device 400. As shown in FIG. 16, the computing device 400 may include a bus 410, one or at least two CPUs 420, a read only memory (ROM) 430, a random access memory (RAM) 440, a communication port 450 connected to a network, an input/output component 460, a hard disk 470, and the like. A storage device (e.g., the ROM 430 or the hard disk 470) in the computing device 400 may store instructions corresponding to at least one selected from a group consisting of the data similarity determination method, the training method of a neural network for determining the data similarity, and the similar object search method provided by at least one embodiment of the present disclosure, and various related data or files. The computing device 400 may also include a human-computer user interface 480.

Of course, the architecture shown in FIG. 16 is only exemplary, and when implementing different devices, one or at least two components of the computing device shown in FIG. 16 can be omitted according to actual requirements.

At least one embodiment of the present disclosure also provides a patient similarity determination method, which includes: acquiring at least one type of medical text data and medical image data of a first patient; acquiring at least one type of medical text data and medical image data of a second patient; mapping one of the medical text data of the first patient and the medical image data of the first patient as a first semantic representation in a semantic comparison space, where the semantic comparison space enables a similarity between a semantic representation obtained by mapping data of a medical image to the semantic comparison space and a semantic representation obtained by mapping data of a medical text to the semantic comparison space to be computed; mapping one of the medical text data of the second patient and the medical image data of the second patient as a second semantic representation in the semantic comparison space; and calculating a similarity between the first patient and the second patient based on at least the first semantic representation and the second semantic representation.

For example, the medical text data may be the medical text data of any patient (for example, one selected from a group consisting of the first patient and the second patient), and the medical image data may be the medical image data of any patient (for example, the other selected from the group consisting of the first patient and the second patient).

For example, acquiring at least one type of the medical text data and medical image data of the first patient comprises: acquiring the medical image data of the first patient and the medical text data of the first patient; acquiring at least one type of the medical text data and the medical image data of the second patient comprises: acquiring the medical image data of the second patient and the medical text data of the second patient; mapping one of the medical text data of the first patient and the medical image data of the first patient as the first semantic representation in the semantic comparison space, comprises: mapping the medical text data of the first patient as the first semantic representation in the semantic comparison space; mapping one of the medical text data of the second patient and the medical image data of the second patient as the second semantic representation in the semantic comparison space comprises: mapping the medical text data of the second patient as the second semantic representation in the semantic comparison space; the patient similarity determination method also comprises: mapping the medical image data of the first patient as a third semantic representation in the semantic comparison space, and mapping the medical image data of the second patient as a fourth semantic representation in the semantic comparison space; the medical text data of the first patient and the medical image data of the first patient both comprise a semantic describing a first characteristic of the first patient, and the medical text data of the second patient and the medical image data of the second patient both comprise a semantic describing a second characteristic of the second patient; and calculating the similarity between the first patient and the second patient based on at least the first semantic representation and the second semantic representation, comprises: acquiring the similarity between the first patient and the second patient based on the first semantic representation, the second semantic representation, the third semantic representation, and the fourth semantic representation.

For example, acquiring the similarity between the first patient and the second patient based on the first semantic representation, the second semantic representation, the third semantic representation, and the fourth semantic representation, comprises: calculating at least one of a similarity between the first semantic representation and the fourth semantic representation and a similarity between the second semantic representation and the third semantic representation.

For example, the similarity between the first patient and the second patient is equal to a sum of the similarity between the first semantic representation and the fourth semantic representation, the similarity between the second semantic representation and the third semantic representation, a similarity between the first semantic representation and the second semantic representation, and a similarity between the third semantic representation and the fourth semantic representation.

For example, the medical text data of the first patient is mapped as the first semantic representation and the medical text data of the second patient is mapped as the second semantic representation by using a first neural network; and the third sub-data is mapped as the medical image data of the first patient and the medical image data of the second patient is mapped as the fourth semantic representation by using a second neural network.

It should be noted that, the first patient, the second patient, the medical text, the medical image, the medical text data of the first patient, the medical image data of the first patient, the medical text data of the second patient, the medical image data of the second patient, the first semantic representation, the second semantic representation, the third semantic representation, the fourth semantic representation, the first neural network, the second neural network, and the similarity between the first patient and the second patient, which are involved in the patient similarity determination method provided by at least one embodiment of the present disclosure, are respectively the same as or similar to the first object, the second object, the first modality, the second modality, the first sub-data, the third sub-data, the second sub-data, the fourth sub-data, the first semantic representation, the second semantic representation, the third semantic representation, the fourth semantic representation, the first neural network, the second neural network, and the similarity between the first data and the second data, which are involved in the data similarity determination method provided by at least one embodiment of the present disclosure. Therefore, for the specific steps of the patient similarity determination method provided by at least one embodiment of the present disclosure, reference may be made to the data similarity determination method provided by at least one embodiment of the present disclosure, and the repeated parts will not be described in detail here.

The patient similarity determination method provided by at least one embodiment of the present disclosure may further include related steps of the training method of a neural network used for the patient similarity determination method. The specific contents of the training method of the neural network used for the patient similarity determination method can refer to the training method of the neural network used for the patient similarity determination method provided by at least one embodiment of the present disclosure, and the repeated parts will not be described in detail here.

At least one embodiment of the present disclosure also provides a training method of a neural network used for a patient similarity determination method, and the training method comprises: acquiring medical text data and medical image data of a training patient, where both the medical image data of the training patient and the medical text data of the training patient comprise a training sub-semantic describing a training characteristic of the training patient; mapping the medical text data of the training patient as a first training semantic representation in a semantic comparison space through a first neural network, where the semantic comparison space enables a similarity between a semantic representation obtained by mapping the data of the medical text to the semantic comparison space and a semantic representation obtained by mapping the data of the medical image to the semantic comparison space to be computed; mapping the medical image data of the training patient as a second training semantic representation in the semantic comparison space through a second neural network; and calculating a similarity between the first training semantic representation and the second training semantic representation, and adjusting parameters of at least one of the first neural network and the second neural network according to the similarity between the first training semantic representation and the second training semantic representation.

It should be noted that, the training patient, the medical text data of the training patient, the medical image data of the training patient, the first neural network, the second neural network, the semantic comparison space, the first training semantic representation, the second training semantic representation, and the similarity between the first training semantic representation and the second training semantic representation, which are involved in the training method of the neural network used for the patient similarity determination method provided by at least one embodiment of the present disclosure, are the same as or similar to the training object, the first training sub-data, the second training sub-data, the first neural network, the second neural network, the semantic comparison space, the first training semantic representation, the second training semantic representation, and the similarity between the first training semantic representation and the second training semantic representation, which are involved in the the training method of a neural network used for determining a data similarity provided by at least one embodiment of the present disclosure, respectively. Therefore, the specific steps of the training method of the neural network used for the patient similarity determination method provided by at least one embodiment of the present disclosure can refer to the training method of the neural network used for determining the data similarity provided by at least one embodiment of the present disclosure, and the repeated parts will not be described in detail here.

At least one embodiment of the present disclosure also provides a similar patient search method, which includes: acquiring at least one type of medical text data and medical image data of a first patient; acquiring at least one type of medical text data and medical image data of each of a plurality of second patients; calculating a similarity between the first patient and each second patient by using any patient similarity determination method provided by at least one embodiment of the present disclosure to obtain a plurality of patient similarities; and outputting information of a second patient corresponding to a patient similarity with a largest value among the plurality of patient similarities.

For example, the similar patient search method provided by at least one embodiment of the present disclosure is similar to the similar object search method provided by at least one embodiment of the present disclosure. The similar patient search method can refer to the similar object search method provided by at least one embodiment of the present disclosure, and the repeated parts will not be described in detail here.

Figure 17:
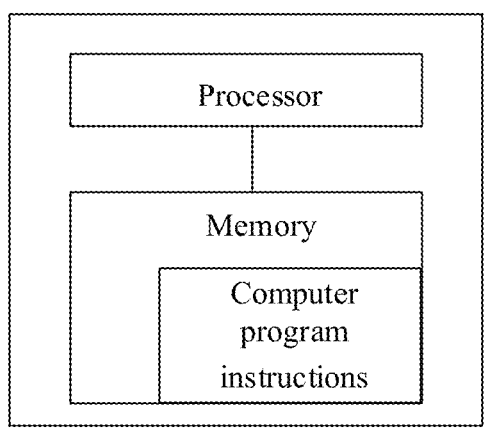
FIG. 17 is an exemplary block diagram of an electronic device provided by at least one embodiment of the present disclosure.

At least one embodiment of the present disclosure also provides an electronic device, as shown in FIG. 17, the electronic device includes a processor and a memory. The memory stores computer program instructions, which can be executed by the processor, and in the case where the computer program instructions are executed by the processor, the processor executes at least one method selected from a group consisting of any patient similarity determination method provided by at least one embodiment of the present disclosure, any training method provided by at least one embodiment of the present disclosure, and any similar patient search method provided by at least one embodiment of the present disclosure.

For example, the electronic device can be implemented as the patient similarity determination device. In this case, in the case where the computer program instructions are executed by a processor, the processor executes any patient similarity determination method provided by at least one embodiment of the present disclosure.

For example, the electronic device can be implemented as the training device of the neural network used for the patient similarity determination method. In this case, in the case where the computer program instructions are executed by a processor, the processor will execute any training method of the neural network used for the patient similarity determination method provided by at least one embodiment of the present disclosure.

For example, the electronic device can be implemented as the patient similarity determination device. In this case, the computer program instructions are executed by a processor, the processor will execute any patient similarity determination method provided by at least one embodiment of the present disclosure.

For example, the electronic device can be implemented as any combination of the patient similarity determination device, the training device of the neural network used for the patient similarity determination method, and the patient similarity determination device. In this case, the processor executes different kinds of methods in different time periods.

For example, in the case where the electronic device is implemented as the patient similarity determination device and the training device of the neural network used for the patient similarity determination device, in a first time period, the processor executes any patient similarity determination method provided by at least one embodiment of the present disclosure; and in a second time period that does not overlap with the first time period in time, the processor executes any training method of the neural network used for the patient similarity determination method provided by at least one embodiment of the present disclosure.

Although the present disclosure has been described in detail above with general descriptions and specific implementation, however it is obvious to those skilled in the art that some modifications or improvements can be made based on the embodiments of the present disclosure. Therefore, these modifications or improvements made without departing from the spirit of the present disclosure all belong to the scope of protection claimed by the present disclosure.

What have been described above are only exemplary implementations of the present disclosure and are not intended to limit the protection scope of the present disclosure, and the protection scope of the present disclosure is determined by the appended claims.

What is claimed is:

1. A data similarity determination method, comprising:
acquiring first data of a first object, wherein the first data comprises first sub-data of a first modality and third sub-data of a second modality;
mapping the first sub-data as a first semantic representation in a semantic comparison space, wherein the semantic comparison space enables a similarity between a semantic representation obtained by mapping data of the first modality to the semantic comparison space and a semantic representation obtained by mapping data of the second modality to the semantic comparison space to be computed;
acquiring second data of a second object, wherein the second data comprises second sub-data of the first modality and fourth sub-data of the second modality;
mapping the second sub-data as a second semantic representation in the semantic comparison space; and
calculating a similarity between the first data and the second data based on at least the first semantic representation and the second semantic representation;
the first object comprises a first characteristic, the first sub-data comprises a first sub-semantic describing the first characteristic, and the third sub-data comprises a third sub-semantic describing the first characteristic;
the second object comprises a second characteristic, the second sub-data comprises a second sub-semantic describing the second characteristic, and the fourth sub-data comprises a fourth sub-semantic describing the second characteristic;
the method further comprises:
mapping the third sub-data as a third semantic representation in the semantic comparison space and mapping the fourth sub-data as a fourth semantic representation in the semantic comparison space; and
calculating the similarity between the first data and the second data based on at least the first semantic representation and the second semantic representation, comprises:
acquiring the similarity between the first data and the second data based on the first semantic representation, the second semantic representation, the third semantic representation, and the fourth semantic representation;
wherein the similarity between the first data and the second data is equal to a weighted sum of a similarity between the first semantic representation and the fourth semantic representation, a similarity between the second semantic representation and the third semantic representation, a similarity between the first semantic representation and the second semantic representation, and a similarity between the third semantic representation and the fourth semantic representation.

2. The data similarity determination method according to claim 1, wherein the first modality is a text, and the second modality is an image.

3. The data similarity determination method according to claim 1, wherein acquiring the similarity between the first data and the second data based on the first semantic representation, the second semantic representation, the third semantic representation, and the fourth semantic representation, comprises:
calculating at least one selected from a group consisting of the similarity between the first semantic representation and the fourth semantic representation and the similarity between the second semantic representation and the third semantic representation.

4. The data similarity determination method according to claim 3, wherein acquiring the similarity between the first data and the second data based on the first semantic representation, the second semantic representation, the third semantic representation, and the fourth semantic representation, further comprises:
calculating at least one selected from a group consisting of the similarity between the first semantic representation and the second semantic representation and the similarity between the third semantic representation and the fourth semantic representation.

5. The data similarity determination method according to claim 1, wherein the first semantic representation, the second semantic representation, the third semantic representation, and the fourth semantic representation are all expressed as vectors;
a dimension of a vector corresponding to the first semantic representation, a dimension of a vector corresponding to the second semantic representation, a dimension of a vector corresponding to the third semantic representation, and a dimension of a vector corresponding to the fourth semantic representation are equal to each other; and
the similarity $f(p_i, p_j)$ between the first data and the second data is obtained by a following expression:

$$f(p_i, p_j) =$$
$$f((t_i, g_i), (t_j, g_j)) = sim_1(t_i, t_j) + sim_2(t_i, g_j) + sim_2(g_i, t_j) + sim_1(g_i, g_j)$$
$$rt_i = NN1(t_i), rg_i = NN2(g_i), rt_j = NN1(t_j), rg_j = NN2(g_j),$$
$$sim_1(t_i, t_j) = \cos(NN1(t_i), NN1(t_j)) = \cos(rt_i, rt_j) = \frac{rt_i^T \cdot rt_j}{|rt_i||rt_j|},$$
$$sim_1(g_i, g_j) = \cos(NN2(g_i), NN2(g_j)) = \cos(rg_i, rg_j) = \frac{rg_i^T \cdot rg_j}{|rg_i||rg_j|},$$
$$sim_2(t_i, g_j) = \cos(NN1(t_i), NN2(g_j)) = \cos(rt_i, rg_j) = \frac{rt_i^T \cdot rg_j}{|rt_i||rg_j|},$$
$$sim_2(g_i, t_j) = \cos(NN2(g_i), NN1(t_j)) = \cos(rg_i, rt_j) = \frac{rg_i^T \cdot rt_j}{|rg_i||rt_j|},$$

where $p_i$ is the first data, $p_j$ is the second data;
$t_i$ is the first sub-data, $g_i$ is the third sub-data, $t_j$ is the second sub-data, and $g_j$ is the fourth sub-data;
$sim_1(t_i,t_j)$ is a similarity between the first sub-data and the second sub-data;
$sim_1(g_i,g_j)$ is a similarity between the third sub-data and the fourth sub-data;
$sim_2(t_i,g_j)$ is a similarity between the first sub-data and the fourth sub-data;
$sim_2(g_i,t_j)$ is a similarity between the second sub-data and the third sub-data;
NN1 refers to mapping a corresponding sub-data by a first neural network, and NN2 refers to mapping a corresponding sub-data by a second neural network; and
$rt_i$ is the first semantic representation, $rg_i$ is the third semantic representation, $rt_j$ is the second semantic representation, and $rg_j$ is the fourth semantic representation.

6. The data similarity determination method according to claim 1, wherein the first sub-data is mapped as the first semantic representation and the second sub-data is mapped as the second semantic representation by using a first neural network; and the third sub-data is mapped as the third semantic representation and the fourth sub-data is mapped as the fourth semantic representation by using a second neural network.

7. A non-transitory storage medium, comprising computer program instructions stored on the non-transitory storage medium,
wherein in a case where the computer program instructions are executed by a processor, the processor executes the data similarity determination method according to claim 1.

8. A similar object search method, comprising:
acquiring first data of a first object;
acquiring second data of a plurality of second objects;
calculating a similarity between the first object and each second object by using the data similarity determination method according to claim 1 to obtain a plurality of object similarities; and
outputting information of a second object corresponding to an object similarity with a largest value among the plurality of object similarities.

9. A patient similarity determination method, comprising:
acquiring at least one type selected from a group consisting of medical text data and medical image data of a first patient;
acquiring at least one type selected from a group consisting of medical text data and medical image data of a second patient;
mapping one selected from the group consisting of the medical text data of the first patient and the medical image data of the first patient as a first semantic representation in a semantic comparison space, wherein the semantic comparison space enables a similarity between a semantic representation obtained by mapping data of a medical image to the semantic comparison space and a semantic representation obtained by mapping data of a medical text to the semantic comparison space to be computed;
mapping one selected from the group consisting of the medical text data of the second patient and the medical image data of the second patient as a second semantic representation in the semantic comparison space; and
calculating a similarity between the first patient and the second patient based on at least the first semantic representation and the second semantic representation;
acquiring at least one type selected from a group consisting of the medical text data and the medical image data of the first patient comprises: acquiring the medical image data of the first patient and the medical text data of the first patient;
acquiring at least one type selected from a group consisting of the medical text data and the medical image data of the second patient comprises: acquiring the medical image data of the second patient and the medical text data of the second patient;
mapping one selected from the group consisting of the medical text data of the first patient and the medical image data of the first patient as the first semantic representation in the semantic comparison space comprises: mapping the medical text data of the first patient as the first semantic representation in the semantic comparison space;
mapping one selected from the group consisting of the medical text data of the second patient and the medical image data of the second patient as the second semantic representation in the semantic comparison space comprises: mapping the medical text data of the second patient as the second semantic representation in the semantic comparison space;

the patient similarity determination method further comprises:
mapping the medical image data of the first patient as a third semantic representation in the semantic comparison space, and mapping the medical image data of the second patient as a fourth semantic representation in the semantic comparison space,
calculating the similarity between the first patient and the second patient based on at least the first semantic representation and the second semantic representation, comprises:
acquiring the similarity between the first patient and the second patient based on the first semantic representation, the second semantic representation, the third semantic representation, and the fourth semantic representation;
wherein the similarity between the first patient and the second patient is equal to a weighted sum of a similarity between the first semantic representation and the fourth semantic representation, a similarity between the second semantic representation and the third semantic representation, a similarity between the first semantic representation and the second semantic representation, and a similarity between the third semantic representation and the fourth semantic representation.

10. The patient similarity determination method according to claim 9,
wherein the medical text data of the first patient and the medical image data of the first patient both comprise a semantic describing a first characteristic of the first patient, and the medical text data of the second patient and the medical image data of the second patient both comprise a semantic describing a second characteristic of the second patient.

11. The patient similarity determination method according to claim 10, wherein acquiring the similarity between the first patient and the second patient based on the first semantic representation, the second semantic representation, the third semantic representation, and the fourth semantic representation, comprises:
calculating at least one selected from a group consisting of the similarity between the first semantic representation and the fourth semantic representation and the similarity between the second semantic representation and the third semantic representation.

12. A similar patient search method, comprising:
acquiring at least one type selected from a group consisting of medical text data and medical image data of a first patient;
acquiring at least one type selected from a group consisting of medical text data and medical image data of each of a plurality of second patients;
calculating a similarity between the first patient and each second patient by using the patient similarity determination method according to claim 9 to obtain a plurality of patient similarities; and
outputting information of a second patient corresponding to a patient similarity with a largest value among the plurality of patient similarities.

13. An electronic device, comprising a processor and a memory,
wherein the memory stores computer program instructions which are executed by the processor, and in a case where the computer program instructions are executed by the processor, the processor executes the patient similarity determination method according to claim 9.

\* \* \* \* \*